United States Patent
O'Connor et al.

(10) Patent No.: US 11,250,953 B2
(45) Date of Patent: Feb. 15, 2022

(54) TECHNIQUES FOR INTEGRATING PROXY NODES INTO GRAPH-MODEL-BASED INVESTIGATORY-EVENT MAPPINGS

(71) Applicant: C/HCA, Inc., Nashville, TN (US)

(72) Inventors: Niall O'Connor, Somerville, MA (US); Mickey Alan Correll, Cambridge, MA (US); Kathryn Hopkins McGill, Cambridge, MA (US); Luke Connors, Boston, MA (US); Daniel Schlauch, Lexington, MA (US)

(73) Assignee: C/HCA, Inc., Nashville, TN (US)

( * ) Notice: Subject to any disclaimer, the term of this patent is extended or adjusted under 35 U.S.C. 154(b) by 0 days.

(21) Appl. No.: 16/298,914

(22) Filed: Mar. 11, 2019

(65) Prior Publication Data
US 2019/0287680 A1 Sep. 19, 2019

Related U.S. Application Data

(60) Provisional application No. 62/642,420, filed on Mar. 13, 2018.

(51) Int. Cl.
| | |
|---|---|
| *G16H 50/20* | (2018.01) |
| *G06N 20/00* | (2019.01) |
| *G06F 16/901* | (2019.01) |
| *G06K 9/62* | (2006.01) |
| *G06F 16/903* | (2019.01) |

(52) U.S. Cl.
CPC .......... *G16H 50/20* (2018.01); *G06F 16/9024* (2019.01); *G06F 16/90335* (2019.01); *G06K 9/6262* (2013.01); *G06N 20/00* (2019.01)

(58) Field of Classification Search
CPC .......... G06F 16/9024; G06F 16/90335; G16H 50/20; G06N 20/00; G06K 9/6262
See application file for complete search history.

(56) References Cited

U.S. PATENT DOCUMENTS

| | | | | |
|---|---|---|---|---|
| 5,574,828 | A * | 11/1996 | Hayward | G16H 50/20 |
| | | | | 706/45 |
| 6,317,700 | B1 * | 11/2001 | Bagne | G06N 5/025 |
| | | | | 702/181 |
| 9,330,357 | B1 * | 5/2016 | Ferdowski | G06Q 40/00 |
| 9,542,450 | B1 * | 1/2017 | Jacobsson | G06F 16/9535 |
| 9,632,654 | B1 * | 4/2017 | Elassaad | G06F 16/951 |
| 2008/0069437 | A1 * | 3/2008 | Baker | G06K 9/6256 |
| | | | | 382/159 |

(Continued)

FOREIGN PATENT DOCUMENTS

WO 2011/077353 A2 6/2011

OTHER PUBLICATIONS

First Action Interview Pilot Program Pre-Interview Communication dated May 13, 2019, in related U.S. Appl. No. 16/298,748, 4 pgs.

(Continued)

*Primary Examiner* — Neveen Abel Jalil
*Assistant Examiner* — Hubert Cheung
(74) *Attorney, Agent, or Firm* — Kilpatrick Townsend & Stockton, LLP

(57) ABSTRACT

Methods and systems disclosed herein relate generally to generating and using graph models to perform entity-specific mappings to investigatory events. More specifically, data-reliability metrics are used to selectively use proxy nodes in graph-model trajectories during generation of the mappings.

23 Claims, 9 Drawing Sheets

(56) References Cited

U.S. PATENT DOCUMENTS

| | | | |
|---|---|---|---|
| 2008/0082584 A1* | 4/2008 | Jung | G16H 50/20 |
| 2009/0058859 A1 | 3/2009 | Crawford | |
| 2011/0040713 A1* | 2/2011 | Colman | A61B 5/743 |
| | | | 706/16 |
| 2013/0124221 A1* | 5/2013 | Lynn | G16H 50/20 |
| | | | 705/2 |
| 2013/0151277 A1* | 6/2013 | Thiers | G06Q 50/22 |
| | | | 705/2 |
| 2014/0336943 A1* | 11/2014 | Pellini | G06F 19/3456 |
| | | | 702/19 |
| 2015/0046191 A1* | 2/2015 | Futscher de Deus | |
| | | | G06F 19/3456 |
| | | | 705/3 |
| 2017/0185730 A1* | 6/2017 | McIntyre | G06N 20/00 |
| 2018/0052962 A1* | 2/2018 | Van Der Koijk | G06F 19/325 |
| 2018/0075359 A1* | 3/2018 | Brennan | G06N 5/022 |
| 2018/0137247 A1* | 5/2018 | Bore | G16H 50/30 |
| 2018/0197625 A1* | 7/2018 | Lobach | G16H 20/60 |
| 2018/0315505 A1* | 11/2018 | Itu | G16H 50/20 |
| 2019/0005395 A1* | 1/2019 | Dutkowski | G06N 5/022 |
| 2019/0108494 A1* | 4/2019 | Nelson | G06N 20/00 |
| 2020/0013490 A1* | 1/2020 | Rumoro | G06F 16/2365 |
| 2020/0032349 A1* | 1/2020 | Espiritu | G16H 50/20 |
| 2020/0138360 A1* | 5/2020 | Fan | A61B 5/7264 |
| 2020/0357524 A1* | 11/2020 | Chan | G06K 9/623 |

OTHER PUBLICATIONS

First Action Interview Office Action Summary dated Jul. 22, 2019 in related U.S. Appl. No. 16/298,748, 5 pgs.
First Action Interview Pilot Program Pre-Interview Communication dated May 13, 2019 in related U.S. Appl. No. 16/298,541, 4 pgs.
First Action Interview Office Action Summary dated Jul. 23, 2019 in related U.S. Appl. No. 16/298,541, 5 pgs.
Extended European Search Report dated Jul. 2, 2019 in related foreign application No. EU 19162631.6, 76 pgs.
Isern D et al: 11 Computer-based execution of clinical guidelines: A review 11 International Journal of Medical, Informatics, Elsevier Scientific Publishers, Shannon, IR, vol. 77, No. 12, Dec. 1, 2008 (Dec. 1, 2008), pp. 787-808, XP025584756, ISSN: 1386-5056, DOI 10.1016/J.IJMEDINF.2008.05.010.

\* cited by examiner

TECHNIQUES FOR INTEGRATING PROXY NODES INTO GRAPH-MODEL-BASED INVESTIGATORY-EVENT MAPPINGS

CROSS-REFERENCE TO RELATED APPLICATIONS

This application claims the benefit of and the priority to U.S. Provisional Application No. 62/642,420, filed on Mar. 13, 2018, which is hereby incorporated by reference in its entirety for all purposes.

FIELD

Methods and systems disclosed herein relate generally to generating and using graph models to perform entity-specific mappings to investigatory events. More specifically, data-reliability metrics are used to selectively use proxy nodes in graph-model trajectories during generation of the mappings.

BACKGROUND

Investigatory events are frequently used to determine whether an underlying protocol or substance is effective at achieving target results. For a particular investigatory event, a degree to which the target result(s) are achieved can be determined based on (for example) a population assessment of a set of individual results corresponding to a set of entities. However, the target result(s) may pertain to a specific context, such that selection techniques by which the set of entities is defined is important to ensure that the result characterization is accurate. Frequently, entity selection is performed by filtering a larger entity pool using a set of entity-attribute filters as predefined for an event. Due to variation in receipt times, comprehensiveness and definitions of attribute identification across entities, the filtering may be time intensive, of insufficient magnitude and/or imprecise. Consequently, conclusion of a given investigatory event may be delayed and/or results may be biased.

Further, one approach for the filtering is to query a database using the attribute filters (e.g., via a compound query). A query may thus involve determining, for each entity in the entity pool and for each attribute filter, whether the entity's attribute satisfies a filter. This type of comprehensive assessment can be resource and time intensive.

SUMMARY

In some embodiments, a computer-implemented method is provided. A set of configurations for an investigatory event can be detected. A set of criteria groups can be determined for the investigatory event using the set of configurations. For each criteria group of the set of criteria groups, a node in a graph structure can be tagged with an identifier of the investigatory event. The node can be configured with the criteria group. The graph structure can connect a set of nodes via a set of edges. Each edge of the set of edges can connect two nodes of the set of nodes. The set of nodes can include a plurality of end nodes. Each node of the plurality of end nodes can identify an investigatory event. For a particular criteria group of the set of criteria groups, it can be detected that an estimated data-reliability metric associated with a particular node configured with the particular criteria group is below a predefined threshold and a proxy can be defined for the particular node. The proxy can be defined to estimate a processing result of the particular criteria group based on a processing result of another criteria group. Another node of the set of nodes can be configured with the other criteria group. An entity data set can be received. A proxy result can be generated by evaluating the other criteria group using at least part of the entity data set. It can be determined that the entity is eligible for the investigatory event based at least in part on the proxy result. A result can be output that associates an identifier of the entity and an identifier of the investigatory event.

In some embodiments, a system is provided that includes one or more data processors and a non-transitory computer readable storage medium containing instructions which when executed on the one or more data processors, cause the one or more data processors to perform part or all of one or more methods disclosed herein. In some embodiments, a computer-program product is provided that is tangibly embodied in a non-transitory machine-readable storage medium, including instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1A:
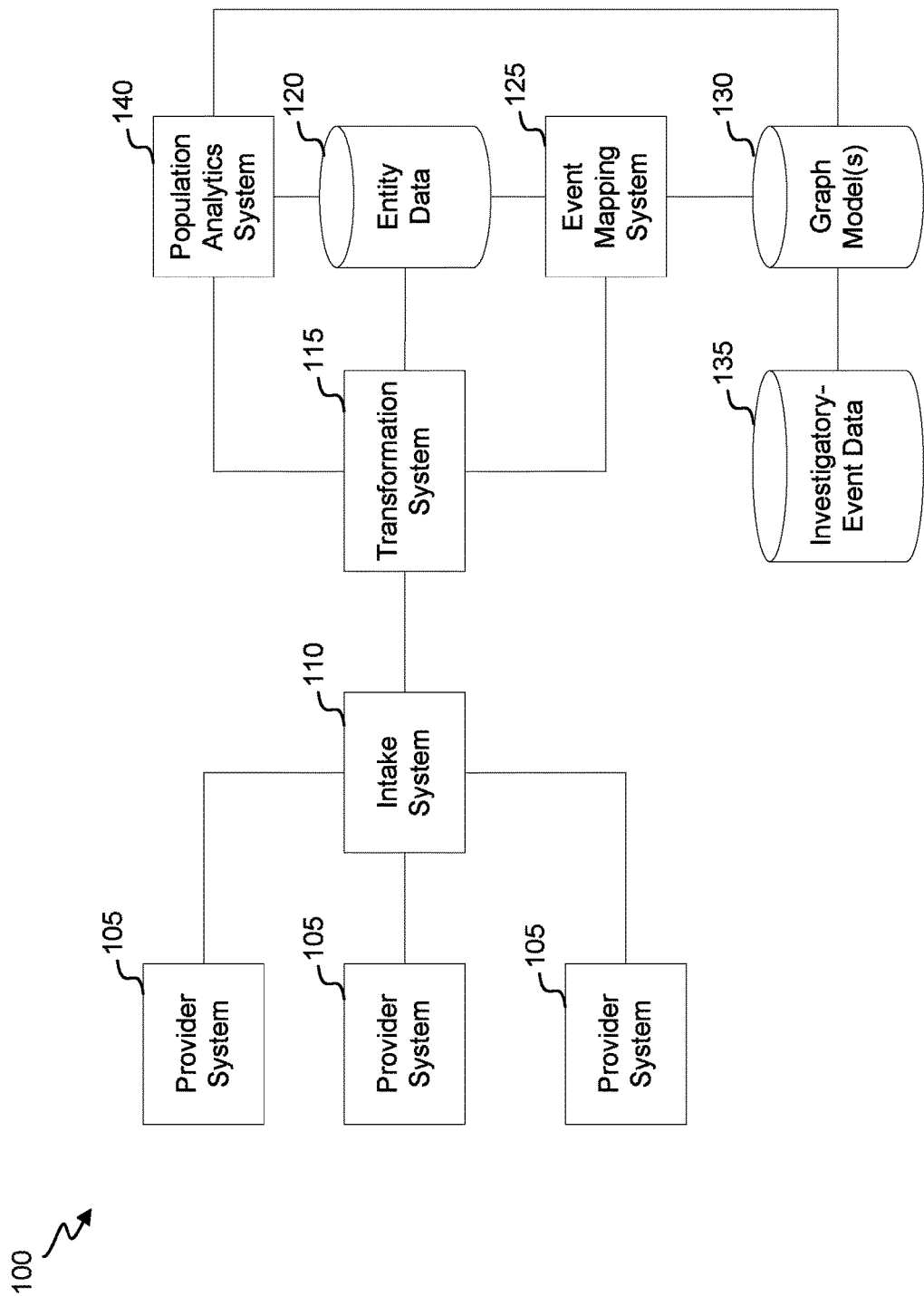
FIG. 1A depicts an exemplary interaction system for processing entity data to generate investigatory-event mappings and population-analytics results.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

In some instances, techniques are provided for generating a graph model to represent various investigatory events. Specifically, a graph model is generated to include, for each of multiple investigatory events, a set of connected nodes that represent criteria for participating in the event. The graph model can then be repeatedly navigated to evaluate, for each entity of a set of entities, in which of the multiple investigatory events the entity is eligible to participate. Specifically, for each entity, a starting point within the graph model can be identified, and criteria represented in first-degree (and subsequent later-degree) connections can be evaluated based on attributes of the entity to determine whether and how far trajectories can extend in a given direction. When an encountered node is a branching node, with different branches corresponding to different investigatory events, a trajectory can replicate such that each resulting trajectory can proceed in its evaluation along one of the branching directions. Each trajectory that extends to an end node can indicate that criteria for an investigatory event represented by the end node are satisfied for the entity.

A graph model can include a complex non-linear graph is generated that represents inclusion and exclusion criteria for an investigatory event. The graph can include a set of nodes and a set of edges. Each node can represent a condition (e.g., disease or ailment), one or more investigatory-event inclusion criteria, one or more investigatory-event exclusion criteria and/or logic operator (e.g., Boolean operator). Each edge can connect two nodes and represents a logical operator (e.g., Boolean operator) and/or relationship between the connected nodes (e.g., that a condition represented by one node is a sub-type of a condition represented by another node). End nodes in the graph can each represent and/or correspond to a specific investigatory event (e.g., specific investigatory event). The graph can then be traversed and processed in accordance with various graph-theory techniques and data representing attributes of individual entities (e.g., semantic codes in an entity record).

Thus, each node represents a condition that evaluates one or more specified types of data (e.g., one or more types of attributes of an entity). An issue may arise, however, if the specified types of data are unavailable, unreliable or inaccurate. Thus, in some instances, techniques are provided to determine, for each of one or more of the set of nodes, an estimated data-reliability metric for the node that indicates an estimated extent and/or frequency to which the type(s) of data are available, reliable and/or accurate. In some instances, the data-reliability metric can be generated based on metadata from one or more entity data sets. The estimated data-reliability metric can include or be based on (for example) an estimate of: a percentage of all entities for which a value of the data type will be available (while generating a trajectory for the entity); a percentage of entities for which a trajectory will advance to a point of evaluating a condition of a given node that depends on data of a particular type and for which data of the particular data is available in an entity data set; an average (or median) confidence of a value of the data type (e.g., corresponding to or being based on sources of values of the data type and/or time periods extending between times at which values was identified and times at which values were evaluated); a statistic characterizing degrees to which format of values of the data type conform with a pre-specified or typical format of a value for the data type; a statistic characterizing degrees to which values of the data type are beyond an average value for the data type, and/or a statistic characterizing a distribution of values for the data type.

For example, a data value that is old (e.g., indicating that it was initially detected or received at least a predetermined period of time ago) and that corresponds to a data type that is likely to or has a substantial potential to change (e.g., within or across the predetermined period of time) in an unpredictable manner, the data value may be deemed to be unreliable. Thus, performing statistics on the age of particular types of data values across entity data sets may serve as an indicator of an overall reliability. As another example, data of a particular data type may be unrepresented and/or absent from at least a predefined threshold percentage or number of entity data sets. Detecting that data of a given type is unrepresented and/or absent may include (for example) identifying a key-value pair having a key that corresponds to the data type and determining that a value of the key-value pair is set to a null value, and/or detecting that data of a given type is unrepresented and/or absent may include querying an entity data set using (for example) a variable name or known data structure to extract the value and receiving a result indicating that no value matching the query constraints was detected.

The data-reliability metric can be assessed to determine whether a reliability condition is satisfied. The reliability condition may be configured to include one or more thresholds (e.g., such that it is satisfied—in various instances—if a numeric threshold exceeds a threshold, is within a range or is below a threshold), one or more specific categories or clusters (e.g., such that the condition is satisfied if the value corresponds to any of the one or more specific categories or clusters), etc.

When the reliability condition is satisfied, the criteria group of the node can be evaluated as configured. When the reliability condition is not satisfied, one or more proxies can be defined for the node. Each proxy of the one or more proxies can include a new or existing node configured with a criteria group that is different compared to the node for which the reliability condition was not satisfied and/or that processes data values that are of one or more data types that are different (e.g., at least partly different or entirely different) than the data type(s) processed by a criteria group for the node for which the reliability condition was not satisfied. The one or more proxies can correspond to multiple criteria nodes (e.g., by including a logic node and multiple other nodes).

As an illustration, it may be determined that a reliability condition is not satisfied for an initial node (having a criteria group configured to be satisfied upon detecting a data value identifying "high stroke risk") due to frequent unavailability of this type of value in entity data sets (e.g., determined by evaluating some or all previously defined entity data sets). A set of other nodes can then be identified as a proxy node: a first proxy node can be configured with a criteria group configured to be satisfied upon detecting blood-pressure values exceeding one or both of a predefined systolic threshold and a predefined diastolic threshold. A second proxy node can be configured with a criteria group configured to be satisfied upon detecting a current prescription of a blood-pressure medication. A third proxy node can be configured with an "OR" criteria group configured to be satisfied when one or both of the criteria group of the first proxy node and the criteria group of the second proxy node is satisfied. The third proxy node may be generated as part of the proxy definition and can be the node most directly integrated into an investigatory-event path, though all of the first, second and third proxy nodes can serve as part of the overall proxy.

The one or more proxies can be identified (for example) using prior trajectory data and/or investigatory-event data identifying entity-selection results. For example, for a data type that was deemed to be frequently unavailable, one or more proxies may be identified by detecting instances in which a value of the data type was present in an entity data set and determining how the value corresponded to values of other data types and/or evaluations of other criteria groups. The determination can be performed (for example) by performing one or more correlations, using a regression technique, performing a clustering algorithm, and/or using another type of artificial-intelligence technique.

As another example, for a data type deemed to be (to at least a predefined degree) unavailable, unreliable or inaccurate, a supervised learning algorithm may be executed using assessment data that indicates—for each individual trial and each of one or more entities—a "true" value of the data type, a "true" result of a criteria group of the node associated with the data type, and/or an indication as to whether the entity was selected for the individual trials (e.g., which may thereby indicate a "true" result of the criteria group on the assumption that the constraint was actually implemented). The true result and/or value may be identified by (for example) extracting the value or result from a communication received from a device associated with the investigatory event; detecting local or remote input from a user authorized in association with the investigatory event; detecting an update to a local or remote data structure associated with the investigatory event. As one illustration, one or more result outputs may be presented at or transmitted to a user device that includes an identifier of each of one or more entities mapped to a particular investigatory event. Corresponding entity data may further be availed. One or more responses may then be detected (e.g., via an interface or by receiving and processing a response communication) that indicates— for each of one, more or all of the one or more entities— whether the entity is selected for the investigatory events. Additionally or alternatively, a communication may be received (e.g., from a user device associated with the investigatory event or from another device) that identifies an updated or new value for the data type.

The true results or values can be used to identify the one or more proxies by determining (for example) which types of data and/or criteria-group outputs (or combinations thereof) are predictive of the "true" results or outputs. It will be appreciated that an initially identified value of a data type itself may be predictive of a true result or value, even if it was initially determined that the data type was inaccurate or unreliable. An assessment may identify a relationship or further constraint that is indicative of whether to use an initial value and/or how to process an initial value. For example, it may be determined that a value is substantially accurate when it falls within a learned range but otherwise is not (e.g., in which case one or more proxies can be identified). The assessment can be performed (for example) by performing one or more correlations, using a regression technique, performing a clustering algorithm, and/or using another type of artificial-intelligence technique (e.g., using a neural network).

Using a graph model can achieve processing efficiency, storage efficiency and improved data insights. For example, one approach to identify which entities correspond to a given investigatory event's criteria is to perform a compound query that includes (for example) an intersection of results returned from multiple underlying queries. This approach can require determining, for each of a large group of entities, whether each criterion of the investigatory event is satisfied based on attributes of the entity. Meanwhile, performing assessment using a graph model can trigger terminating assessments of an investigatory event's criteria in relation to a particular entity upon first detecting that one of the investigatory event's criteria is not satisfied. Thus, processing resources can be conserved and processing time can be reduced.

As another example, one approach to represent investigatory events is to create, for each investigatory event, a data structure (e.g., a data object, table, array, row or column, data file, etc.) that defines criteria for the investigatory event. Thus, as the complexity of the events' criteria sets grow and as the number of investigatory events grow, data-structure storage size expands. This increased data size further can result in a many-times additional storage increase as results are stored from criteria evaluation as it pertains to individual entities. Meanwhile, performing assessment using a graph model can support using a single graph element (e.g., node or edge) to represent a given criteria that may be specified by multiple investigatory events. Thus, not only can this decrease storage space used to represent an investigatory event, but it can also decrease storage space used to store entity-specific evaluations of constraints.

Generating entity-specific trajectories through a graph model representative of investigatory events can further be used to detect data relationships and/or distributions. For example, relationships can be determined by characterizing a degree of connectedness between discrete nodes. If it is determined that results from multiple constraints are highly correlated, a result of one of the multiple constraints may subsequently be estimated, if corresponding entity-attribute data is unavailable, based on a result of another of the multiple constraints.

Further, assessment of trajectories' connections and termination points can be used to generate output pertaining to individual investigatory events that include (for example) a predicted quantity or fraction of entities for which individual or all criteria for the event for which the criterion is satisfied (e.g., for a given time period), a predicted time duration to identify a target number of entities for which all criteria for the event are satisfied; a degree to which each individual criterion of the event's criteria is limiting entities that are deemed to be eligible for the event, etc. The output may trigger a revision to the criteria, which can further preserve processing resources.

In some instances, an investigatory event includes a clinical trial to evaluate (for example) a safety and/or effectiveness of a medical device, drug or therapy at treating a medical condition (e.g., disease) or ailment (e.g., symptom). Constraints associated with the investigatory event may identify attributes of entities (e.g., people) eligible to participate in the trial. An entity's attributes can include and/or an investigatory-event's constraints can specify (for example) one or more particular health characteristics, one or more particular demographic characteristics, one or more particular characteristics of present and/or past treatment, and/or one or more particular characteristics of one or more medical tests. Thus, it will be appreciated that an entity attribute need not identify a present characteristic of the entity (e.g., and may instead characterize a current or past prescribed medication or past disease state). Each of an investigatory event's constraints can (for example) identify one or more thresholds of a numeric characteristic, identify one or more particular categories of a categorical characteristic, include a binary indicator as to whether a particular characteristic is represented as an attribute of the entity, etc. A set of constraints for an investigatory event can include one or more inclusion criterion and/or one or more exclusion criteria. For example, constraints for a given investigatory event can include: diagnosed with diabetes; age between 18 and 45; not having taken a biguanide medication over the last six months, and having normal blood-panel results received within the last month.

It will be appreciated that an investigatory event can include (for example) a single a discrete event (e.g., a one-time treatment or surgery); an extended-duration event (e.g., administration of a multi-week therapy, or administration a week-long and continuous administration of stimulation via a medical device during which a magnitude is adjusted in accordance with a particular stimulation pattern; a multi-month time period during which a particular drug is taken in accordance with a dosing regimen); and/or multiple discrete events (e.g., multiple discrete administrations of a particular therapy; multiple doses of a drug to be taken in a prescribed manner; and/or multiple activations of a medical device to operate in a specific manner). The investigatory event can be defined to relate to a particular hypothesis, to define one or more defined endpoints, and to clearly identify one or more measurables to be collected at the endpoint(s). In some instances, the investigatory event includes and/or corresponds to a particular care-pathway evaluation, which can (for example) identify an order in which different treatments are to be administered, a manner and/or frequency in which a vital sign is to be measured (e.g., taking a blood-pressure measurement on a person's calf instead of arm), etc. The evaluation can be configured (for example) to compare a particular care pathway to another particular pathway or default (e.g., normal) data.

Further details pertaining to graph structures are disclosed in U.S. application Ser. No. 16/298,541, filed on Mar. 11, 2019 and entitled "TECHNIQUES FOR GENERATING INVESTIGATORY-EVENT MAPPINGS USING GRAPH-STRUCTURE TRAJECTORIES" and in U.S. application Ser. No. 16/298,748, filed on Mar. 11, 2019 and entitled "DATA INTEGRATION USING GRAPH STRUCTURES". Each of these applications is hereby incorporated by reference in its entirety for all purposes.

FIG. 1A depicts an interaction system 100 for processing entity data to generate investigatory-event mappings and population-analytics results. A provider system 105 can be associated with a medical care provider (e.g., physicians, nurses, pharmacists, physician offices, hospitals, and/or laboratories). In response to receiving input and/or test result at a given provider system 105, the provider system 105 can transmit electronic data to an intake system 110. The electronic data can identify an entity (e.g., by name, social security number or other identifier). The electronic data can further identify (for example) a diagnosis, test result (e.g., result of a blood, urine, genetic or imaging test), prescription, and/or one or more symptoms. Intake system 110 may parse the electronic data to identify discrete field values and avail the values (in association with the entity identifier) to a transformation system 115. Transformation system 115 can translate codes into attributes, each having a standardized form. It will be appreciated that, in some instances, for at least one field value, no transformation is necessary to accord with the standardized form, such that a corresponding attribute is defined to be the attribute.

The standardized attributes can then be stored in an entity data store 120. The standardized attributes can further be availed to an event mapping system 125. Event mapping system 125 may use entity attributes for an individual entity to generate one or more trajectories throughout a graph model (stored in a graph model data store 130). The graph model can be managed to include criteria associated with open investigatory events, which can be determined using investigatory-event data from an investigatory-event data store 135 (e.g., which may be generated based on similarly processing communications from an investigator or investigatory-event data store to parse and transform information). The graph model and entity data may be stored to rely upon a same set of standardized data fields as fields corresponding to the standardized attributes, such that entity data corresponding to graph-model criteria can be easily identified. When a trajectory ends at an end node corresponding with an investigatory event, event mapping system 125 can transmit data to an entity device or provider system 105 that indicates that the entity is eligible for the investigatory event (e.g., and/or identifies each of multiple investigatory events for which the entity qualifies).

The standardized parameter data can further be availed to a population analytics system 140. Population analytics system 140 may identify (for example) a quantity and/or characteristics of entities that are eligible for particular investigatory events. Population analytics system 140 may characterize sub-populations of various groups (e.g., indicating percentages of a condition-specific entity group that corresponds to various age groups). Population analytics system 140 may further or alternatively use current and past entity data to predict a time period over which, cumulatively, a predefined number of eligible entities for a particular investigatory event will be identified (e.g., in view of the event's criteria). The prediction may further be used to predict a time period during which, cumulatively, a predefined number of entities will enroll in the particular investigatory event.

Event mapping (e.g., performed by event mapping system 125) can begin by identifying a starting node in the graph model based on entity data associated with the entity. For example, one or more starting nodes may be identified for the entity based on data (e.g., entity attributes) associated with the entity in an entity data store. The one or more starting nodes may correspond to (for example) a disease diagnosis or a symptom occurrence and/or one or more other factors (e.g., procedure history, demographic characteristic, family history, genetic-mutation characteristic, etc.). Each rule of the set of applicable rules can include criteria represented by a node and/or edge connected to a starting node of the one or more Edges and nodes connected to the starting node can be evaluated to determine whether the entity matches a corresponding particular inclusion criterion, avoids a corresponding particular exclusion criterion and/or meets a given combination of multiple criteria as defined by logical operator. Each criterion can relate to one or more entity attributes. Entity attributes can be extracts from, identified within and/or determined based on one or more medical records associated with the entity and/or inputs from the entity, a medical care provider or pharmacist. When the criterion is appropriately satisfied (e.g., inclusion criterion is met, exclusion criterion is avoided and/or a logic-operator-defined combination is satisfied) with respect to a given neighboring edge and connected node, a trajectory is initiated that extends to the connected node (extending from the starting node to the connected node). For each initiated trajectory, subsequent edges and nodes are iteratively evaluated to determine whether (and/or how) the trajectory is to extend (and/or branch apart) or whether the trajectory is to terminate.

Each of a set of end nodes represented in the graph model can correspond to a particular investigatory event. Each branch (one or more connected edges and nodes) extending from an end node can represent a criterion for the investigatory event. Thus, for a given entity, one or more starting nodes can be identified based on entity data (e.g., indicating a current condition). With respect to each starting node of the one or more starting nodes, the starting node may be positioned along or an endpoint of one or more investigatory-event-associated branches. For each branch, criteria represented along the branch can be iteratively (e.g., and conditionally) evaluated to determine whether the criteria is satisfied. For each branch extending from an investigatory-event node, a result can be determined for an entity that indicates (for example) one of: that the criteria/criterion of the branch is satisfied, that the criteria/criterion of the branch is not satisfied, an estimate that a criteria/criterion of the branch is satisfied, an estimate that a criteria/criterion of the branch is not satisfied, an estimated probability that a criteria/criterion of the branch is satisfied, an extent to which a criteria/criterion of the branch is satisfied or that the criteria/criterion of the branch was not completely evaluated due to a lack of pertinent entity data points. In some instances, an evaluation of a criteria can be performed to differentiate between instances in which a criterion is determined to be not satisfied based on the appropriate data and instances in which a criterion cannot be evaluated due to an unavailability of at least some data to be assessed using the criterion. For example, a weight associated with a node may be set to 0 if it cannot be assessed due to a lack of available or data but may be set to a negative value if data is available to assess the criterion and it is determined that the criterion is not satisfied. As another example, a weight associated with a node may be correlated with a resolution and/or confidence of data available and being used to assess a criterion.

The criteria evaluation may be conditional in that (for example) whether a trajectory extends to a given node in a branch for a given entity may depend on past results. For example, if a criteria/criterion associated with an earlier node is not satisfied, is not satisfied to a sufficient extent and/or is associated with a below-threshold probability of being satisfied, the trajectory may terminate such that criteria of subsequent nodes of the branch need not and/or will not be assessed for the entity. A score associated with the particular investigatory event and particular entity can be generated based on the results of the criteria assessment. The score may further depend on weighting of various branches. For example, a weight may be determined based on whether satisfaction of an inclusion criterion or clearing of an exclusion criterion is required. As another example, a weight may be determined based on a portion of the population (or a particular type of population) for which the criterion/criteria is satisfied. Investigatory events of potential interest for a given entity may be determined based on the score. For example, an identification of and/or information for each investigatory event associated with a score above a predefined threshold may be transmitted.

In some instances, a graph structure can be used to identify entities for a potential or actual synthetic control arm of an investigatory event. Specifically, the entities can be identified as each entity within a set of entities (e.g., for which a particular type of data is available and/or for which graph-model trajectories were generated within a predefined time period) for which each criteria of the investigatory event is satisfied and an additional constraint is satisfied or for which each criteria of the investigatory event except one or more specific criteria are satisfied. For example, the additional constraint may indicate that the entity has received or is assigned to an investigatory event to receive one of one or more predefined (e.g., standard-of-care) types of treatments. As another example, the one or more specific criteria may be configured to be satisfied when data indicates that the entity is not on a current standard-of-care treatment.

Figure 1B:
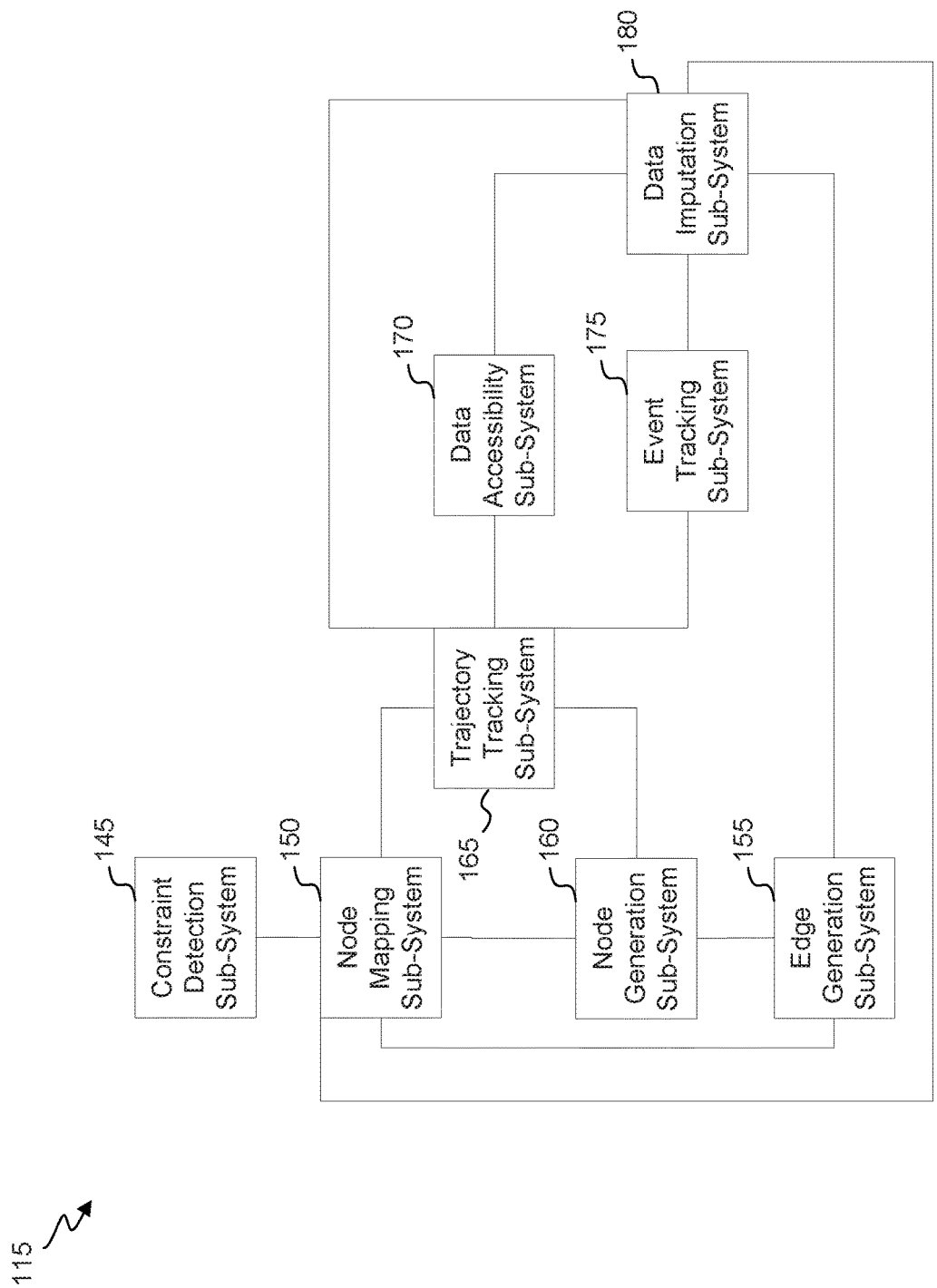
FIG. 1B depicts an exemplary transformation system for transforming electronic data into entity attributes.

FIG. 1B depicts an exemplary transformation system 115 for transforming electronic data into entity attributes. In some instances, part or all of the transformation system depicted in FIG. 1B and/or described in association thereof can be integrated into interaction system 100 depicted in FIG. 1A. Transformation system 115 can include a constraint detection sub-system 145 that detects a constraint associated with a new or newly modified investigatory event. The constraint may be included in a criteria group specified for the event. The constraint may be identified (for example) from input received over a network and/or via an interface and/or data included in a file (e.g., uploaded file) or electronic transmission. The constraint may relate to one or more entity attributes. The constraint may indicate that a condition is satisfied when (for example) a given attribute is set to a specified value; a given attribute is detected in entity data and/or a given attribute is within a specified open or closed range.

A node mapping sub-system 150 can perform a targeted or general query pertaining to a graph model to determine whether the graph model includes a node having a criteria-group constraint corresponding to the detected constraint. In some instances, node mapping sub-system 150 determines that a criteria-group constraint of an existing node corresponds to the detected constraint if, and only if, the condition constraint is an exact match to the detected constraint. In some instances, node mapping sub-system 150 determines that a criteria-group constraint of an existing node corresponds to the detected constraint if the constraints overlap (e.g., by at least a threshold amount). For example, the constraints may be mapped when (e.g., and only when) a range or specified-value list of the criteria-group constraint includes at least a designated fraction (or all) of a range or specified-value list of the detected constraint. As another example, the constraints may be mapped when (e.g., and only when) a range or specified-value list of the detected constraint includes at least a designated fraction (or all) of a range or specified-value list of the criteria-group constraint.

In instances in which a corresponding node is identified for a detected constraint, the corresponding node can be included in a path corresponding to the (e.g., new or modified) investigatory event. For example, metadata can be associated with the node that associates the node with an identifier of the investigatory event. Further, an edge generation sub-system 155 can generate one or more edges to connect the corresponding node to other (new or existing) nodes in the path corresponding to other constraints pertaining to the investigatory event.

In instances in which a corresponding node is not identified for a detected constraint, a node generation sub-system 160 can generate a new node that corresponds with a criteria group including the detected constraint. Further edge generation sub-system 155 can generate a plurality of edges, each of which can be configured such that one end of the edge connects to the new node and another end of the edge connects to another node (e.g., another new node or an existing node in the graph model). In some instances, node generation sub-system 160 generates multiple new nodes to represent the detected constraint, and edge generation sub-system 155 can generate a plurality of nodes to integrate the multiple new nodes into the graph model. For example, a constraint may indicate that a criteria group is satisfied when a given attribute is equal to any of three specified values. In some instances, this constraint may be represented by a single node. In some instances, this constraint may be represented by four nodes: three nodes that represent each of the three specified values and a fourth "OR" node.

Transformation system 115 can further be configured to configure graph models and constraint integration based on empirical and/or predicted availability of various types of data. For example, if a constraint relates to a type of entity attribute that is rarely (or never) included in entity data sets, is subjective, is a high-order descriptor and/or is difficult (or impossible) to detect, integration of a representation of the constraint may be performed to account for these practicalities. One illustration of a high-order descriptor is that an entity is of normal weight.

For example, transformation system 115 can include a trajectory tracking sub-system 165 that tracks trajectory data in association with particular nodes (e.g., a new node or a node to which a constraint is mapped). The trajectory data may indicate (for example) a number or fraction of trajectories that terminated at the node. This assessment may specifically indicate a number or fraction of entity representations for which a criteria group of the node was determined not to be satisfied. For example, if a criteria group of a node indicates that an age of an entity is to be between 18 and 65, the number or fraction may indicate a number or fraction of instances for which this criterion was evaluated using entity-specific data and was determined to be satisfied. The trajectory data may be determined (for example) by querying a trajectory data structure, querying a node-centric data structure, query an edge-centric data structure, and/or assessing one or more densities of trajectories (e.g., at a position closer to a starting node and at a position at or extending from the evaluated node).

In some instances, prior assessments and/or trajectories can provide criteria-group information that extends beyond a binary analysis. For example, the information may indicate whether entity data to be evaluated by the criteria group was available and/or a confidence of this data. A data accessibility sub-system 170 may determine this information by (for example) querying an existing entity data set and/or querying one or more other data structures or data sources for one or more particular types of data in association with the entity. Data accessibility sub-system 170 may identify a confidence of data based on (for example) a date on which the entity data to be evaluated by the criteria group was initially declared or defined, a system that initially declared or defined the entity data to be evaluated, a degree to which a field corresponding to the entity data to be evaluated matches a type of data as specified in the criteria group, etc. For example, if a criteria group relates to a stage of a disease, data accessibility sub-system 170 may identify a confidence metric associated with this type of data as being low if entity data identifying a stage is more than a predefined threshold time period old.

A rule (e.g., pertaining to a graph model in its entirety, pertaining to a specific node and/or pertaining to a specific investigatory event) may specify an effect that data unavailability or sub-optimal data confidence is to have on a trajectory. For example, a rule may indicate that a trajectory is to terminate or that a trajectory is to connect to the node (e.g., potentially while storing an indication of the data unavailability or decreased data confidence). In some instances, a trajectory is to extend across all paths connected to a starting node associated with an entity, but criteria-group results are to be stored and then aggregated across the path in a particular manner to determine whether individual investigatory events are matches for the entity.

Transformation system 115 can further include an event tracking sub-system 175, which can identify—for each end node (and thus for each investigatory event)—the entities accepted for the investigatory event. For example, user input may be locally received or detected via a communication transmitted by a user device. The user input may include a list of entity identifiers selected for the event and/or may indicate, for each of a set of entities, whether the entity was selected for the event.

A data imputation sub-system 180 can process the event-tracking data and trajectory data to impute or to infer a particular type of entity data (e.g., a meta-variable) and/or an evaluation of a particular criteria group based on one or more other types of entity data and/or one or more other evaluations of one or more other criteria groups. The imputation or inference may be performed (for example) for entity-data types that are unavailable or associated with a low confidence at least a predefined threshold number or percentage of times. In some instances, a general determination is made as to which types of data for which an imputation is to be performed. In some instances, an imputation is performed on an entity-specific basis (e.g., such that an imputation is performed or used in response to detecting that a particular type of entity data is unavailable or associated with a low data-confidence metric).

In some instances, in order to determine which types of data to use for the imputation and/or how to use the data for the imputation, data imputation sub-system 180 may (for example) fit a regression model, train a machine-learning model or perform a correlation to determine an extent to which entity data types (e.g., that are frequently available, frequently associated with high data confidence, available for a particular entity being assess and/or associated with high data confidence for a particular entity being assessed) are predictive of whether the entity will be selected for an investigatory event (or are predictive across an entity population of the data type being imputed or a result of a criteria-group assessment relating to the data type being imputed). For example, data imputation sub-system 180 may determine that a time since diagnosis and an initial disease stage identified at diagnosis can be used to impute a current disease stage.

In some instances, data imputation sub-system 180 can assess trajectories that intersect individual nodes to update each of one, more or all nodes in a graph model to be associated with a (e.g., new or updated) probability that reflects a likelihood that (for example) satisfaction of a criteria group associated with the node is predictive of one or both of: reaching an end node that terminates a path along which the node is positioned and being selected for an investigatory event associated with an end node that terminates a path along which the node is positioned. Further or additionally, data imputation sub-system 180 can assess trajectories that extend along paths that intersect individual nodes to update each of one, more or all nodes in a graph model to be associated with a (e.g., new or updated) probability that reflects a likelihood that (for example) one or more attribute-value characterizations and/or one or more results of assessment of criteria group(s) of one or more nodes positioned closer to a starting node along a path is predictive of a result of an evaluation of a criteria group of the node. Thus, the graph model may be a probabilistic graph model. These probabilities may be used to (for example) impute entity-data values in response to missing data, determine whether to accept entity-data values when they are associated with low confidence metrics and/or assign a weight to a result of a criteria-group evaluation for the node.

In some instances, data imputation sub-system 180 can assess trajectories that intersect individual nodes to update each of one, more or all nodes in a graph model to be associated with a (e.g., new or updated) probability that reflects a likelihood that (for example) satisfaction of a criteria group associated with the node is predictive of one or both of: reaching an end node that terminates a path along which the node is positioned and being selected for an investigatory event associated with an end node that terminates a path along which the node is positioned. Further or additionally, data imputation sub-system 180 can assess trajectories that extend along paths that intersect individual nodes to update each of one, more or all nodes in a graph model to be associated with a (e.g., new or updated) probability that reflects a likelihood that (for example) one or more attribute-value characterizations and/or one or more results of assessment of criteria group(s) of one or more nodes positioned closer to a starting node along a path is predictive of a result of an evaluation of a criteria group of the node. Thus, the graph model may be a probabilistic graph model. These probabilities may be used to (for example) impute entity-data values in response to missing data, determine whether to accept entity-data values when they are associated with low confidence metrics and/or assign a weight to a result of a criteria-group evaluation for the node.

In some instances, an imputation can trigger a change or addition to a graph model. For example, a node that corresponds to the constraint group for which data is being imputed can be mapped to one or more other nodes that relate to criteria groups for which assessments are used for the imputation. As another example, metadata corresponding to the node that corresponds to the constraint group for which data is being imputed can identify how other entity data can be used to estimate the entity data to be assessed at the node (e.g., when the entity data is unavailable and/or is associated with low confidence and/or all of the time).

Figure 2:
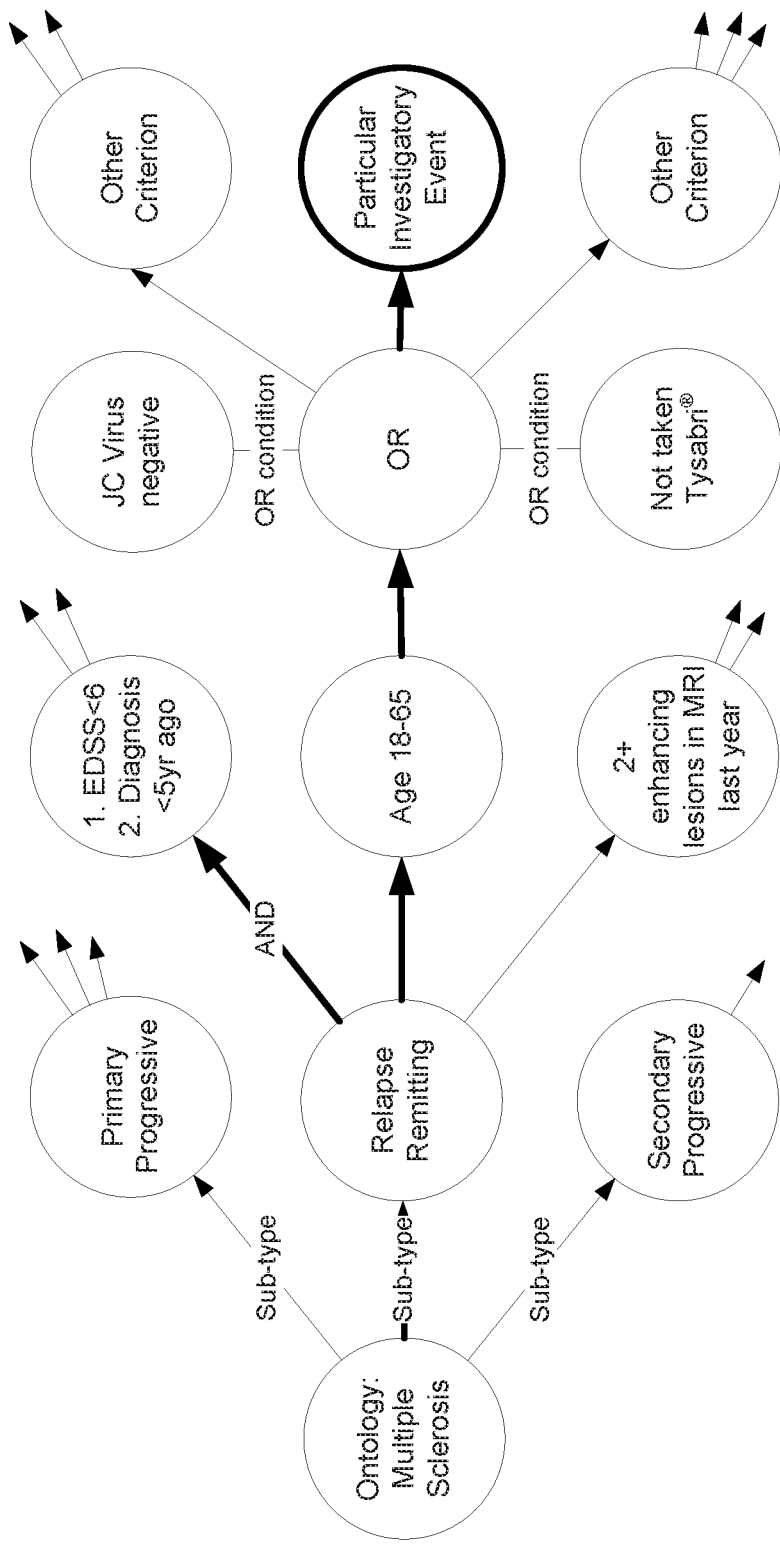
FIG. 2 shows an example of a portion of a graph model and trajectories associated with a given entity's data record.

FIG. 2 shows an example of a portion of a graph model and trajectories associated with a given entity's data record. In this instance, the entity's data record indicates that the entity has an autoimmune disease, such that the "Ontology: Autoimmune Nervous System Disorder" is identified as a starting node. In this example, the entity's data record does not explicitly identify a type of the autoimmune nervous system disorder, such that specific data is not available to assess the "Ontology: Multiple Sclerosis" node. The trajectory assessment can store an indication of the missing data but proceed along the trajectory.

Further, the entity's data record indicates that a disease stage is "Relapse Remitting", such that the Relapse-Remitting sub-type node is also identified as a starting node. This particular coded stage can be coded as a type of multiple sclerosis. Thus, even though the entity's data record does not specifically indicate that the entity has multiple sclerosis, the graph's indication that multiple sclerosis is a super-type of the relapse-remitting type supports a high-confidence estimate that the entity has multiple sclerosis, which can then also (or alternatively) serve as a starting node.

Identifying a starting node for an entity can include (for example) comparing condition-identifying data associated with the entity to each of a set of condition-identifying nodes in the graph model. In some instances, a given node may include multiple names (e.g., and one or more abbreviations) that may be used to refer to a same condition. Thus, the criterion associated with the node may be that data indicating an entity-specific condition matches (or matches to at least a predetermined degree) a condition identifier associated with the node.

In some instances, a particular criterion can be grouped with one or more other criteria for collective evaluation of the criteria within the group. Various criteria within the group may, but need not, relate to different types of field values and/or entity-data types relative to each other. In some instances, a criteria group includes only a single criterion (e.g., if a given criterion is not to be collectively evaluated with one or more other criteria).

A criteria-group score may be assigned to the criteria group that relates to an estimation as to whether a given criteria group is satisfied with respect to a particular entity. The score may be based on whether and/or a degree to which entity data matches or otherwise accords with (e.g., is within a designated range) the relapse-remitting criterion and/or a confidence in estimating that a criteria-evaluation result is accurate. For example, a given criteria group may indicate an entity is to be between 24 and 55 years old. An entity's age may be available in entity data, such that this criterion can be assessed to produce a binary result. However, if a birth date is not present and/or an indication as to when the age data was provided, a confidence may be less than 100%. A score may then be generated to be a sub-optimal result. As another example using the same criterion, entity data may lack information indicating an age of an entity, but an age may be estimated (e.g., based on a listed profession, health metrics, etc.). A confidence of the age may be generated based on the data fields used to generate the estimate, a consistency as to which age brackets various data-field values correspond, etc. The score can then be generated based on the estimate and confidence.

In some instances, a score may further or alternatively indicate an extent to which entity data indicates that the entity is eligible for the investigatory event. Thus, even if criteria groups for multiple groups are all clearly satisfied with high certainly, the criteria groups may be assigned different scores. For example, a score may depend on population data indicating how frequently the criteria group (or a part of the criteria group) is satisfied. When few entities satisfy the criteria, yet the entity is amongst the few, the score may be higher relative to criteria commonly satisfied. The criteria-group score may further or alternatively be based on a weight assigned to the criteria (or a part of the criteria) by a user associated with the investigatory event.

In some instances, rather than included multiple criteria in a single node, whether a trajectory extends in a given direction may depend on criteria assessments performed in accordance with multiple nodes of the graph model. Node groupings can be effected (for example) by associating logic operators with edges connecting the nodes and/or with the nodes themselves. For example, FIG. 2 depicts a node that indicates that an "OR" logic operator is to be effected by determining whether the entity is at least one of: having avoided taking Tysabri® and being JC virus negative.

If the entity's data record does not include medication data and/or data indicating whether the entity has the JC virus, node data may indicate that this criteria cannot be evaluated. The criteria-group score for the corresponding group (associated with the "OR" node) may be assigned a lower value than if data had been available and had indicated that the criteria was satisfied. In some instances, the criteria-group score for the corresponding node (associated with the "OR" node) may be assigned a higher value than if data had been available and had indicated that the criteria was not satisfied.

Thus, a criteria-group score can be generated for each criteria group associated with the particular investigatory event. A score for the entity-event pair can then be generated based on the aggregated criteria-group scores. For example an entity-event score may be generated by summing or averaging criteria-group scores. In some instances, various criteria-groups are assigned corresponding weights (e.g., as indicated by user input to reflect an importance of satisfying a criteria group, based on population data, etc.), and an entity-event score may be generated by performing a weighted sum.

By representing data for multiple investigatory events in this graph format, a single graph model can be used repeatedly for many entities and at multiple points in time. The graph model can then facilitate reducing or eliminating processing that requires evaluation of investigatory-event criteria for a large list of diseases to be repeatedly integrated with entity-specific data structures and/or that requires repeatedly retrieving disease and entity data. Not only can this efficient representation reduce the space required for the graph model, but further, a given individual node and/or edge may be part of multiple branches associated with multiple investigatory events. Thus, a single evaluation of a criteria for the individual node and/or edge can be used during evaluation of multiple investigatory events. Further, various potential trajectories can be evaluated using different machines, such that parallel processing is enabled.

Figure 3:
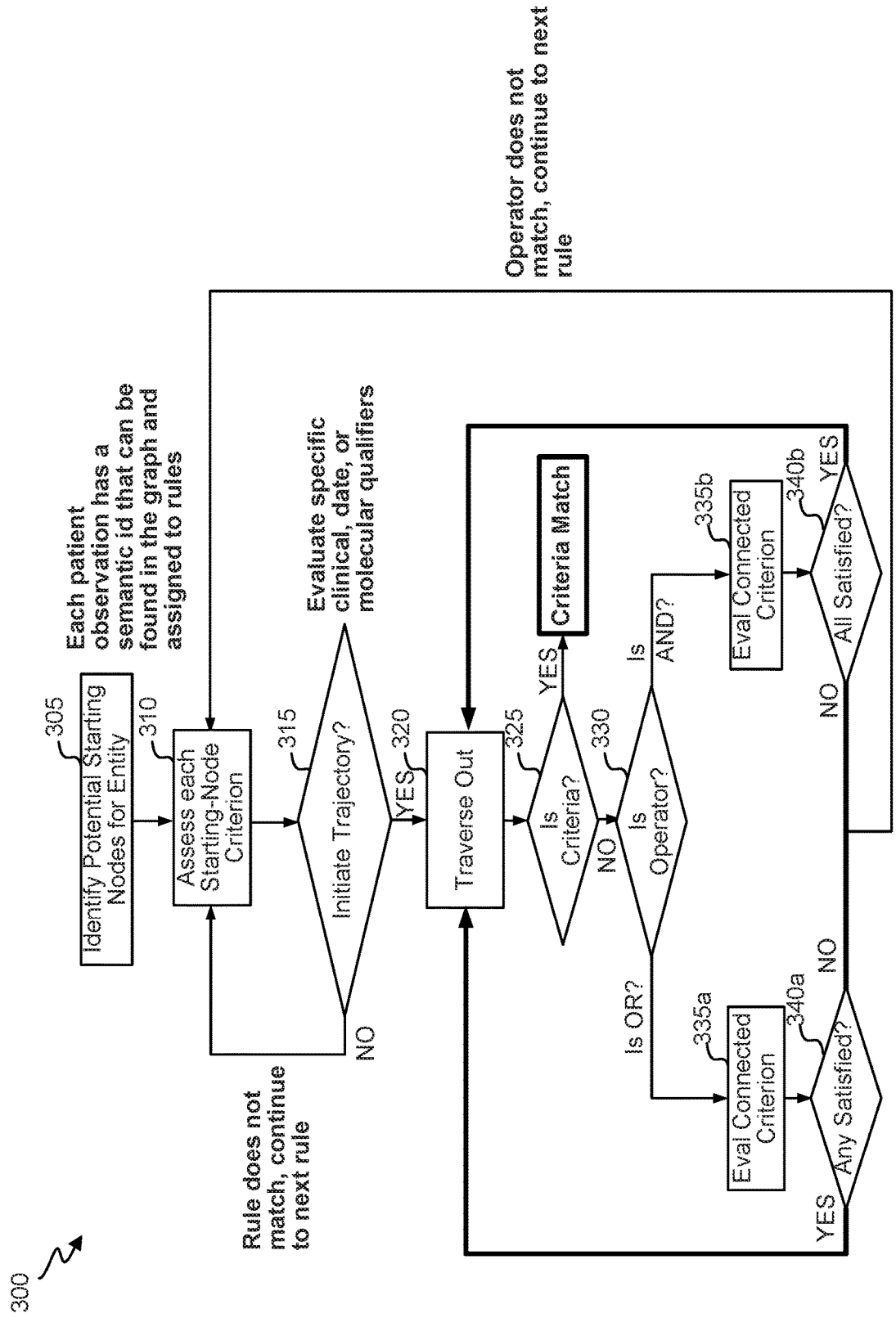
FIG. 3 shows a process for using a graph model to identify investigatory-event matches for an entity.

FIG. 3 shows a process 300 for using a graph model to identify investigatory-event matches for an entity. At block 305, one or more starting nodes within a graph model are identified that pertain to key-value pairs associated with a particular entity. For example, electronic data for an entity may include one or more semantic identifiers (e.g., included in one or more key-value pairs), each of which can represent a physical characteristic or category thereof. A semantic identifier can represent (for example) a disease, medical condition, ailment, age, weight, and so on. An incomplete subset of a set of nodes in a graph model can be designated (e.g., via metadata) as starting nodes, each of which can be associated with a semantic identifier (e.g., included in a criterion or criteria group of the node).

The one or more starting nodes can be identified as each starting node for which one, more or all of the semantic identifiers identified in a criteria group of the starting node are also present in the entity data. In some instances, the one or more starting nodes are identified as each starting node for which one, more or all of the criteria includes a constraint on a value type (e.g., as indicated by a corresponding semantic code) that is also present in the entity data. For example, the one or more starting nodes may include a starting node having a constraint: "symptom=blindness" if entity data includes any key-value pair that includes a key corresponding to (or set to) "symptom". In some instances, the one or more starting nodes are identified as each starting node for which one, more or all of the criteria includes a constraint that specifies a value type or a value (e.g., via a corresponding semantic code) that is also present in the entity data. Thus, in the above example, the one or more starting nodes may include the exemplary starting node so long as the entity data included any semantic code (e.g., as part of a key or as part of a value) that corresponded to (or that was set to) "symptom" or "blindness". In some instances, the one or more starting nodes are identified as each starting node for which one, more or all of the criteria includes a specific constraint that is also present in the entity data. Thus, in the above example, the one or more starting nodes may include the exemplary starting node so long as the entity data included a semantic code (e.g., as part of a value) that corresponded to "blindness".

Notably, the identification of the one or more starting nodes need not be performed by assessing criteria associated with all nodes in a graph model. Rather, nodes designated as starting nodes can be selectively assessed. A node may be designated as a starting node in response to (for example) detecting an input corresponding to an indication that a criterion or criteria group of the node is a fundamental focus of one or more investigational events (e.g., in association with inputs initially defining the one or more investigational events); determining (e.g., based on population data or past trajectory data) that a criterion or criteria group of the node is the most limited amongst criteria associated with one or more investigational events); and/or determining that an edge of at least one investigatory-event branch is positioned at the node. The one or more starting nodes may (for example) include an incomplete subset of the starting nodes in the graph model, such as only those starting nodes for which there is overlap (e.g., and possibly complete overlap) between the semantic identifier(s) included in the criteria group of the starting nodes and the electronic data of the entity.

Thus, for example, a first starting node may be identified that includes a criterion requiring a diagnosis a particular disease (as indicated by a first semantic identifier) that is also included in the entity data, and another starting node may be identified that corresponds to an age constraint (e.g., such that each of the other starting node and the entity data include a semantic identifier indicating that a corresponding value or specification relates to an age data type).

At block 310, for each of the one or more starting nodes, each criterion associated with the starting is assessed using the entity data to determine whether to initiate a trajectory from the starting node in association with the entity. In some instances, a mere match of the semantic identifiers is sufficient to identify a starting node (e.g., which a semantic identifier match included matching a semantic identifier specified in a constraint of a single criterion with a semantic identifier in the entity data). In some instances, an entity-data value associated with the semantic identifier is to be further assessed in accordance with one or more criteria of the starting node. For example, a criterion may indicate that an entity is not to merely have any age but is to be 18 years old or older.

At block 315, for each of the one or more starting nodes, it is determined whether to initiate a trajectory from the starting node in association with the entity. It can be determined to initiate the trajectory if it is determined, at block 310, that the criteria group of the starting node is satisfied. Conversely, it may be determined that the trajectory is not be initiated if it is determined, at block 310, that the criteria group of the starting group is not satisfied.

If the trajectory is initiated, process 300 proceeds to block 320 to traverse out from the starting node. The outward traversal can extend along an edge included in an investigatory-event branch and that is connected to the starting node. In some instances, one, more or all edges in a graph model are directional, such that a trajectory only extends along an edge having that connects to a present node with a receiving end and that points to another node. In some instances, a single starting node may serve as a starting node for multiple investigatory-event branches. In these instances, when the branches diverge (e.g., at the starting node or at another node), a trajectory may split or a duplicate trajectory may be generated that can be assigned to one of the diverging edges while an initial trajectory can be assigned to another of the diverging edges.

At block 325, it is determined whether the edge and other node represent a criterion or criteria group. If so, the criterion or criteria group can be evaluated via the assessment depicted in a process 400 depicted in FIG. 4. If not, process 300 continues to determine whether the edge and other node represent one or multiple specific operators at block 330. Each of the specific operators may include a logical operator or Boolean operator.

In the depicted instance, if the edge and other node represent an "OR" operator, process 300 continues to block 335a, at which the criteria (or criteria groups) connected to the operator and evaluated. For example, the other node may be connected to multiple nodes, each of which represent a criteria group (including one or more criteria). At least one (or all) of the criteria group can be evaluated (e.g., in a manner similar to the processing depicted in FIG. 4) to determine whether any criterion of the criteria group are satisfied.

At block 340a, it is determined whether any of the connected criteria (or criteria groups) connected to the operator are satisfied. If so, process 300 can return to block 320, such that the trajectory can be further extended. Otherwise, the trajectory can terminate, and process 300 can return to block 310 to assess another of the one or more starting nodes (or process 300 can end if there are no remaining starting nodes of the one or more starting nodes).

In the depicted instance, if the edge and other node represent an "AND" operator, process 300 continues to block 335b, at which the criteria (or criteria groups) connected to the operator and evaluated. For example, the other node may be connected to multiple nodes, each of which represent a criteria group (including one or more criteria). All criteria of the criteria group can be evaluated (e.g., in a manner similar to the processing depicted in FIG. 4), potentially individually, to determine whether the criteria are satisfied. At block 340b, it is determined whether all of the connected criteria (or criteria groups) connected to the operator are satisfied. If so, process 300 can return to block 320, such that the trajectory can be further extended. Otherwise, the trajectory can terminate, and process 300 can return to block 310 to assess another of the one or more starting nodes (or process 300 can end if there are no remaining starting nodes of the one or more starting nodes).

To reduce duplicate processing, data from individual traversals of the graph model can be saved in association with an entity identifier. For example, a binary result can be stored in association with each node of one or more nodes to indicate whether a criteria group of the node was satisfied with respect to a given entity. As another example, a past graph trajectory can be saved. The trajectory can indicate that multiple criteria groups associated with multiple nodes along the trajectory were satisfied and potentially an indication as to whether a criteria group associated with an end node of the trajectory was satisfied. This data can allow a next iteration to skip analysis of at least some criteria group, which may relate to one or more other investigatory events. In some instances, each node can be associated with an indication as to what types of entity data are evaluated. When a new communication or entity record indicates that a particular type of entity data has been updated since a previous evaluation of a given criteria group that relies upon the particular type of entity data, a new assessment may be performed for a previously evaluated node associated with the criteria group. In some instances, a saved result indication (e.g., indicating a result of evaluation of a criteria group) or saved trajectory can have an expiration time period or date, such that node evaluations performed subsequent to the time period or date are to be performed again and/or such that a new retrieval of entity data is to be performed to evaluate the associated criteria group(s).

As a result of time-synchronized processing or discrete processing, evaluations corresponding to a single node in a graph model can be performed for many entities using the entities' corresponding entity codes. For each of these entities, a respective evaluation can indicate whether a criterion specified in association with the node was satisfied. Further, for each of these entities, one or more other characteristics of the entity may be determinable (e.g., based on electronic entity data). Thus, the cross-entity evaluations can be used to generate one or more statistics or distribution that correspond to the node-associated criterion. As one example, a statistic can be generated that indicates a percentage of all of the many entities (or a specified sub-group of the many entities) for which a criteria group was satisfied. As another example, a distribution can be generated for a variable (e.g., value in a key-value pair) that is assessed in the criteria group. The statistic and/or distribution may be useful to inform an investigatory-event investigator as to an impact that a corresponding criterion may have on a size of a population that is eligible for an investigatory event.

In some embodiments, a graph model is used to generate population analytics that may be used to characterize an ongoing study or inform the definition of criteria for a new investigatory event. For example, previous traversal data through a part of the graph model can indicate a portion or number of entities for which a particular criterion or type of criteria or criteria group was satisfied, which may be used to predict an impact that a same or similar particular criterion, type of criteria or criteria group would have in terms of identifying eligible entities for an investigatory event. The prediction may include (for example) a number of entities for which the criterion will be satisfied during a predefined time period (or time period identified via input from an investigator user) or a time period required to identify at least a predefined threshold number of entities for which the criterion is satisfied.

Figure 4:
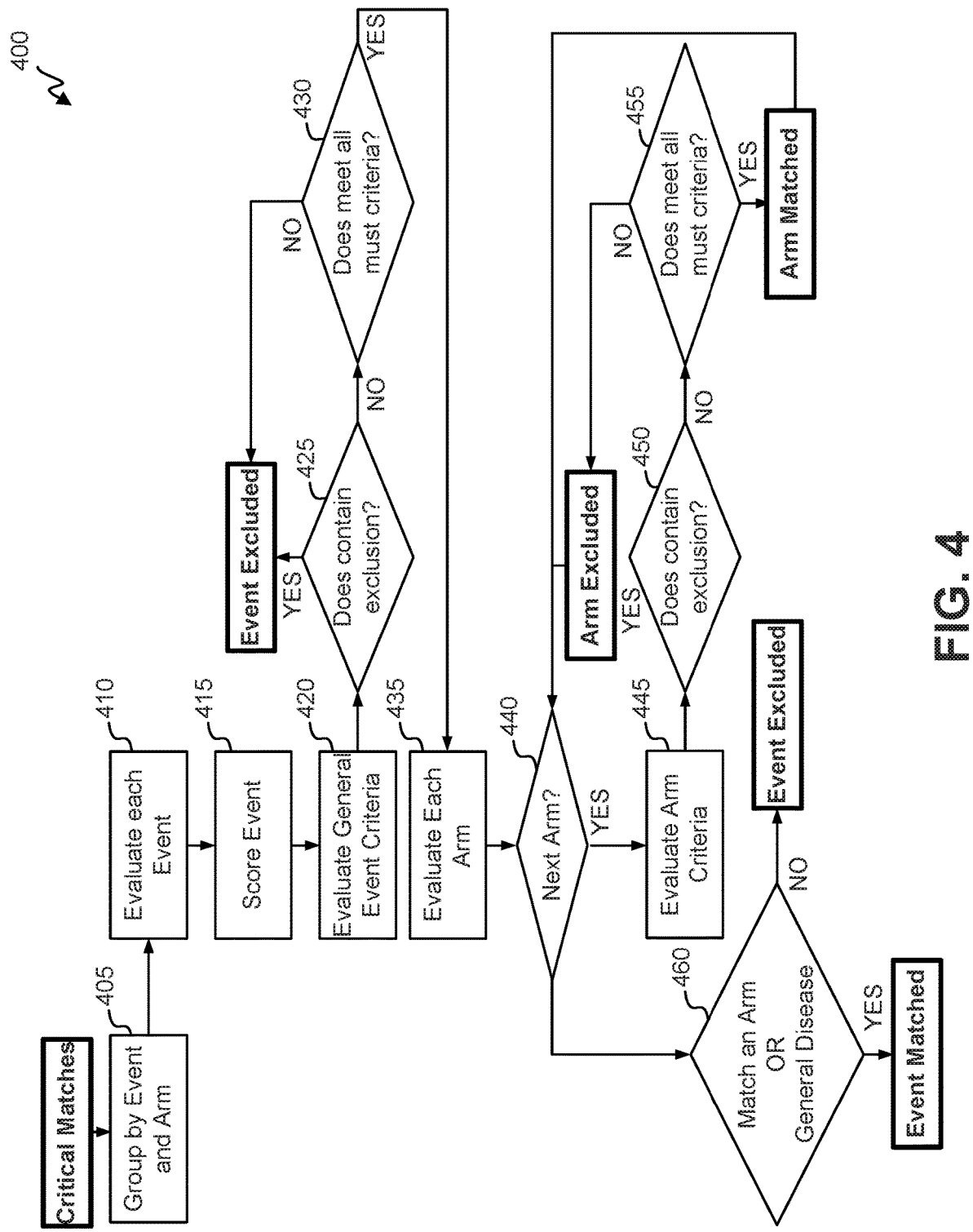
FIG. 4 shows process for evaluating criteria in accordance with some embodiments.

FIG. 4 shows process 400 for evaluating criteria in accordance with some embodiments. At block 405, criteria from one or more rules (corresponding to one or more investigatory events and one or more arms) to be evaluated for an entity is collected and (if applicable) separated by investigatory event and/or arm. At block 410, a processing is initiated to assess criteria for each particular investigatory event's rule(s). At block 415, a score is generated for a given investigatory event. The score can depend on which data elements corresponding to a investigatory event are present in entity data. For example, an investigatory event may be associated with a criterion relating to a CT scan. If data for the specified type of CT scan is absent from an entity record, it may negatively influence a score. An extent to which it negatively influences a score may depend on a weight associated with the criteria.

At block 420, general investigatory-event criteria is evaluated. The general investigatory-event criteria can include (for example) one or more inclusion criteria and/or one or more exclusion criteria. Each criteria may have been defined based on user input. User input may further indicate, for each of one or more of the criteria, that the criterion is to be an absolute exclusion criterion (or an absolute inclusion criterion). User input may indicate that each of one or more criteria is to be neither an absolute exclusion criterion or absolute inclusion criterion (or a lack of an indication that that a criterion is to have either absolute designation may provide this information). Evaluating a criterion can include identifying entity data that corresponds to the criterion and determining—based on the entity data—whether the criterion is satisfied. At block 425, it is determined whether a result of the evaluation includes an exclusion (that is, whether an exclusion criterion was satisfied). If so, the investigatory even can be eliminated as a possible match for the entity. Otherwise, process 400 proceeds to block 430 where it is determined whether all "must" criteria were met via the evaluation. If not, the investigatory event can be eliminated as a possible match for the entity. Otherwise, process 400 proceeds to block 435.

In some instances, an investigatory event may have distinct criteria for different arms in a study. In these instances, arm-specific processing is initiated at block 435. At block 440, a first arm is identified, and criteria for the arm are evaluated using entity data at block 445. At block 425, it is determined whether a result of the evaluation includes an exclusion (that is, whether an exclusion criterion was satisfied). If so, the arm is excluded and process 400 proceeds to block 440, where it is determined whether the investigatory event includes another arm for which to evaluate criteria. Otherwise, process 400 proceeds to block 455 where it is determined whether all "must" criteria were met via he evaluation. If not, the arm is excluded. Otherwise, the arm is identified as a match. In either instance, process 400 returns to block 440, where it is determined whether the investigatory event includes another arm for which to evaluate criteria. When each arm has been assessed, process proceeds to block 460, where it is determined whether an arm and/or the general investigatory event was identified as a match or possible match for an entity.

Figure 5:
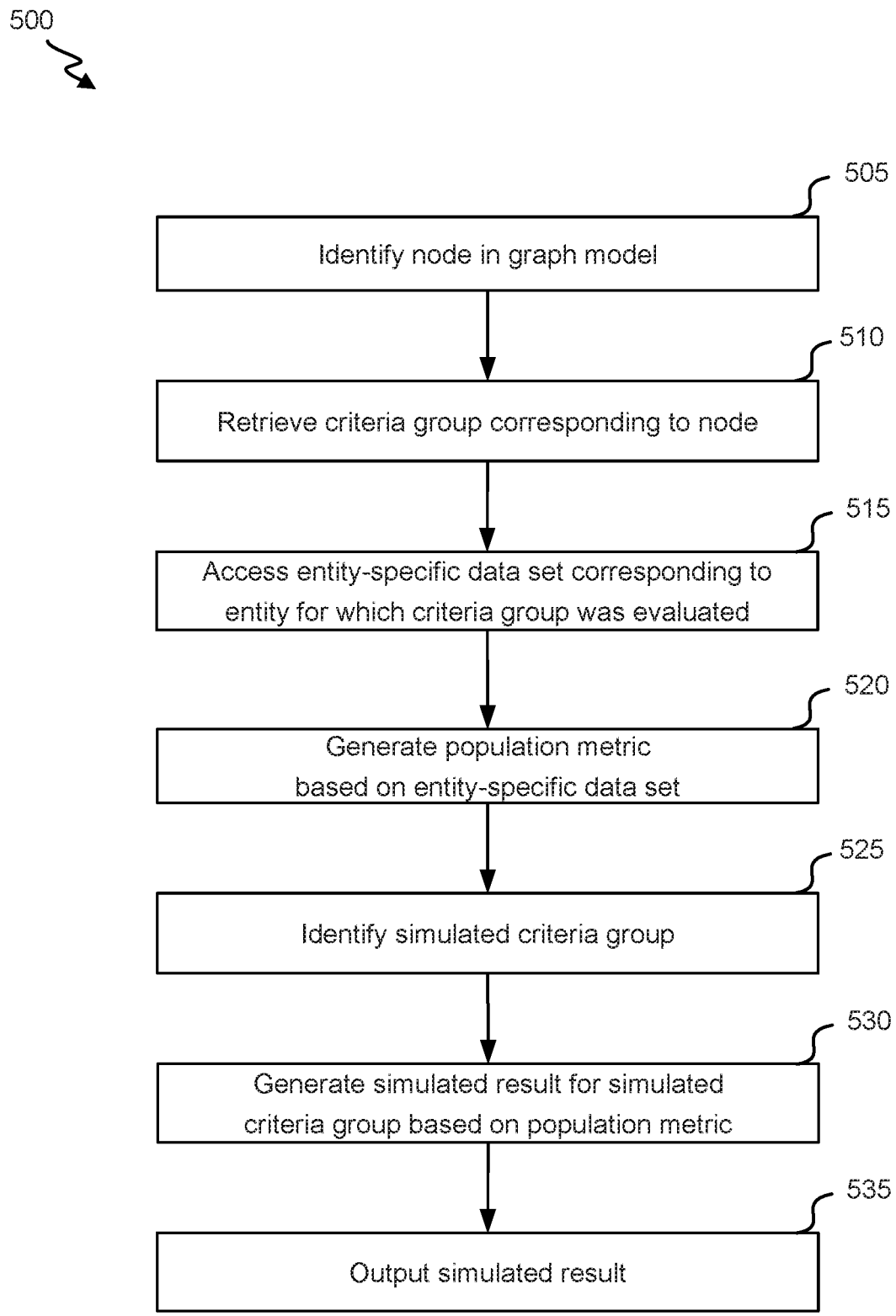
FIG. 5 shows a flowchart of a process for generating a simulated result based on graph-model iterations in accordance with some embodiments.

FIG. 5 shows a flowchart of a process 500 for generating a simulated result based on graph-model iterations in accordance with some embodiments. Process 500 begins at block 505 where a node in a graph model is identified. The graph model can include a set of nodes and a set of edges. Each edge of the set of edges can connect two nodes of the set of nodes. The graph model can be configured such that a trajectory extends to a next node when a criteria group (e.g., including a single criterion or multiple criteria) specified by the next node and/or a criteria group (e.g., including a single criterion or multiple criteria) specified by a connecting edge is satisfied. The graph model can include a plurality of end nodes. Each end node of the plurality of end nodes can identify an investigatory event (e.g., via a coded identifier of the event). The graph model can include a model that relates to multiple diseases, medical conditions and/or symptoms.

The node can include one associated with a criteria group relating to one or more particular types of entity characteristic(s). The particular characteristic can include one (for example) identified (via input) by a user and/or included in a preliminary or actual criteria group for a new investigatory event. In some instances, criteria groups associated with each of a plurality of nodes in the graph model are identified, and the criteria groups are then filtered with respect to a given entity based on whether entity data for the entity includes each type of the particular type(s) of entity characteristic(s) identified in the criteria group. Thus, the node identified at block 505 can include one corresponding to one or more entity-characteristic types that are also included in the entity data.

In some instances, the particular characteristic(s) can be defined as (for example) corresponding to a particular type of characteristic and a particular constraint for the characteristic type. The particular characteristic(s) can be defined (for example) based on input provided at a webpage, such as a selection of a characteristic type from amongst multiple types of characteristics includes in a list or pull-down menu, typing an code for a characteristic type in a text field, typing a specific value or value threshold in a text field, or identify a threshold for a value of the characteristic using a slider input tool As other examples, the characteristic type and/or constraint can be determined by extracting the information from a file or received communication. In some instances, identification of a given constraint is made in accordance with a standardized format (e.g., to require an identifier of a characteristic type to be one of a predefined list of characteristic-type identifiers). The input, file and/or communication may have been associated with a user coordinating and/or involved with selecting entities for a given investigatory event or a user with authorization to define or modify the graph model.

It will be appreciated that a single node can correspond to criteria applicable to multiple investigatory events. Associating a given investigatory event with a node may be performed in an automatic or semi-automatic manner. For example, one or more inputs or files may be received that identify a set of criteria groups (e.g., each including one or more criteria) to be assessed (e.g., sequentially assessed in an identified order, sequentially assessed in an order to be automatically determined or concurrently assessed). An event mapping system may then determine, for each of the set of criteria groups (or each criterion within the set of criteria groups), whether an existing node in a graph model corresponds to a same (or similar within a defined degree) criteria group (or criterion). If so, an identifier of the investigatory trial can be linked to an identifier of the node. If not, a new node can be generated that corresponds to the criteria group (or criterion).

The node identification performed at block 505 can include identifying a starting node for which the criteria group is satisfied based on particular entity data. A node in the graph model may be designated as a starting node if it is a first node in a path terminating at an end node (e.g., and thus for which an edge corresponding to a given investigatory event extends from the node but no edge corresponding to the given investigatory event extends from another node to the node). Edges between the event-associated nodes can be formed (for example) when each criteria group is mapped to a new or existing node (or as the mapping is occurring). In some instances, an edge can be multi-purposed to apply to the investigatory event in addition to one or more other investigatory events. Nodes can be connected with edges in accordance with a particular protocol. For example, edges may be generated such that criteria groups are evaluated in an order corresponding to a predicted degree to which a criteria group will filter an entity group (e.g., such that edges are formed to cause more restrictive criteria groups being evaluated before less restrictive criteria groups). As another example, edges may be generated such that criteria groups are evaluated in an order corresponding to indicated importances of various criteria groups that pertain to an investigatory event (e.g., as conveyed via input and/or such that edges are formed to cause more important criteria groups to be evaluated before less important criteria groups). As yet another example, edges may be generated such that criteria groups are evaluated in an order corresponding to predicted availability of entity data to be assessed by the criteria groups (e.g., such that edges are formed to cause criteria groups associated with higher predictions of data availability to be evaluated before criteria groups associated with lower predictions of data availability).

At block 510, a criteria group that corresponds to the node is retrieved (e.g., by querying a data store using an identifier of the node). The criteria group can include (for example) one or more criteria—each of which can identify a type of entity characteristic and constraint on the same. The criteria group can include a constraint associated with the particular type of characteristic. For example, the node may have been identified due to the criterion relating to age, and block 510 can determine that the criteria group for the node specifies that an entity's age must be between 18 and 30. Notably, in instances in which block 505 includes identifying a node as one that relates to a particular characteristic in a (preliminary or actual) criteria group associated with a new investigatory event, a constraint on the particular characteristic as set forth in the criteria group for the new investigatory event need not be the same as a constraint on the particular characteristic as set forth in a criteria group associated with the node.

At block 515, entity-specific data is accessed. More specifically, iteration data that includes a set of entity-specific data points can be accessed. Each entity-specific data point in the entity-specific data can correspond to an entity for which the criteria group has been evaluated, and each entity-specific data point can correspond to the criteria group. For example, an entity-specific data point can include a binary indication as to whether the criteria group (or a criterion within the criteria group) was satisfied for the corresponding entity. As another example, the entity-specific data point can include an entity characteristic used in an evaluation of whether the criterion was satisfied. The entity-specific data may correspond to iteration data associated with a single investigatory event or iteration data associated with multiple investigatory events (e.g., each of which are associated with the criteria group).

The entity-specific data point may further include related information, such as a time at which the criterion was evaluated. Notably, the set of entity-specific data points need not only include data points corresponding to entities for which the criterion was satisfied.

At block 520, a population metric is generated based on the iteration data. The population metric can include a distribution or statistic based on the set of entity-specific data points. In some instances, the population metric can include a percentage of entities for which the criteria group was satisfied and/or a rate at which criteria-group satisfaction was detected for individual entities. In some instances, the population metric includes a distribution, characteristic of a distribution, or a statistic of the characteristic (across all of the data points, across the data points associated with satisfaction of the criteria group, and/or across the data points associated with the criteria group not being satisfied). The statistic can include (for example) a mean, median, mode, variance, standard deviation or range.

At block 525, a simulated criteria group is identified. The simulated criteria group can be the same or different than the retrieved criteria group. The simulated criteria group can include one used to identify the node in block 505. The simulated criteria group can include a preliminary or actual criteria group of new investigatory event. The simulated criteria group can be based on a constraint on a same type of characteristic as associated with the criteria group for the identified node (e.g., and one identified as a preliminary or actual criteria group of a new investigatory event). The constraint may include a same or different constraint (e.g., one or more same or different thresholds) than the constraint in the criteria group for the identified node.

At block 530, a simulated result is generated for the simulated criteria group based on the population metric. Generating the simulated result can include performing an extrapolation or interpolation technique. Generating the simulated result can include generating a distribution and/or model based on values of the characteristic in the entity-specific data set, and identifying a number or percentage associated with a constraint of the simulated criterion based on the distribution and/or model. The simulated result may, but need not, correspond to a same type of variable as the population metric. The simulated result may include (for example) a predicted percentage of an entity population for which the simulated criteria group will be satisfied, a predicted time period of identifying a predefined number of entities for which the simulated criteria group will be satisfied, and/or a predicted number of entities within an entity population for which the simulated criteria group will be determined to be satisfied within a predefined time period.

In some instances, the simulated result also depends on one or more other simulated criteria groups. For example, a simulated investigatory even may include a set of simulated criteria groups (with each simulated criteria group of the set of simulated criteria groups including one or more criteria)—one of which is the simulated criteria group. The simulated result may then identify (for example) a predicted percentage of an entity population who will be eligible for and/or accepted to the simulated investigatory event, a predicted time period of identifying a predefined number of entities who will be eligible for and/or accepted to the simulated investigatory event, and/or a predicted number of entities within an entity population who will be eligible for and/or accepted to the simulated investigatory event within a predefined time period.

At block 535, the simulated result is output. For example, the simulated result can be presented at a local or remote interface and/or transmitted to another device. The simulated result may be presented concurrently with an option to modify the simulated criteria group. Detecting a modification can trigger part or all of process 500 to be repeated. In some instances, an interface presents a high-level simulated result that corresponds to a predicted number or percentage of entities that correspond to all criteria groups identified for a preliminary or actual investigatory event and further identifies—for each individual criteria group identified for the event—a degree to which the individual criteria group is limiting the predict number of percentage relative to the other criteria groups. This further identification can be conveyed (for example) by presenting, in association with a representation of each criteria group, a number, color, size, or text descriptor that indicates a degree to which it is contributing to overall limiting of a size of a simulated result.

In some instances, a graph model can be used to iteratively evaluate whether a specified mutation is detected. The iterative analysis can include first determining whether a particular type of mutation has been observed and then identifying whether the mutation occurs within a particular region (e.g., of the genome, epigenome, etc.) or an assessment performed in the reverse order. In some instances, a graph model can be used to represent class-level constructs, such as molecular alteration groups. For example, directionality of edges can facilitate representing an ordered series of molecular alterations (e.g., with respect to a set of nodes).

Figure 6:
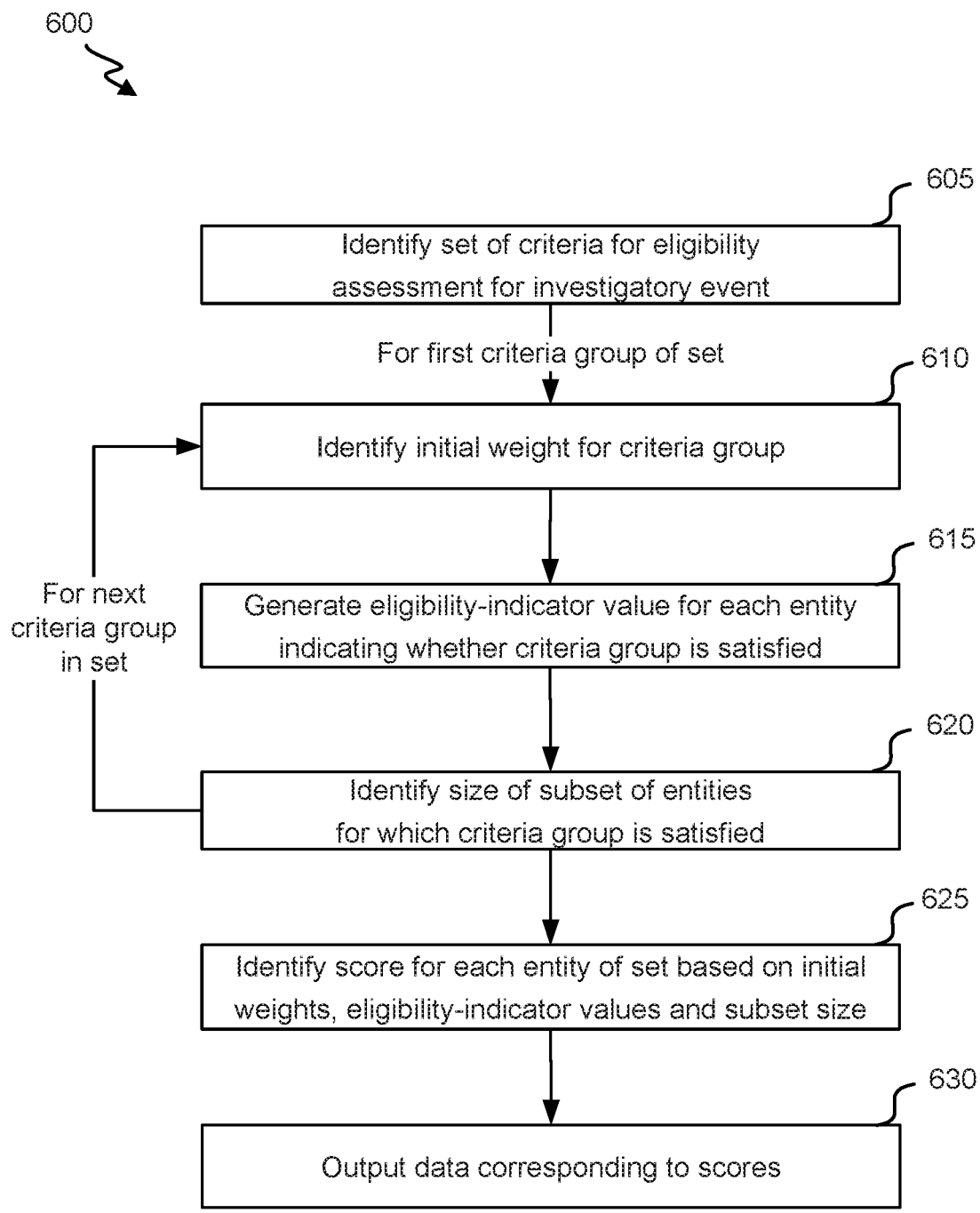
FIG. 6 shows a flowchart of a process for generating entity-specific scores indicative of a degree of match to criteria in accordance with some embodiments.

FIG. 6 shows a flowchart of a process 600 for generating entity-specific scores indicative of a degree of match to criteria in accordance with some embodiments. Process 600 begins at block 605 where a set of criteria corresponding to an eligibility assessment for a particular investigatory event is identified. The set of criteria may include (for example) each criteria in each criteria group that is associated with the investigatory event. (It will be appreciated that, in some instances, individual criteria groups may be evaluated instead of or in addition to each individual criterion.) In some instances, each of at least one of the criteria is not an eligibility requirement but is instead an eligibility factor. For example, the criterion may relate to comorbidity. An investigator may prefer that the entity not have multiple health issues but may stop short of conditioning acceptance on the presence of a single condition. As another example, the criterion may relate to prescriptions previously used to treat a condition. In various instances, it may be desirable to recruit entities not having used any or many other prescriptions, or it may be desirable to recruit entities having previously used multiple other prescriptions (e.g., which were been ineffective). Assessment of each criterion of the set of criteria may generate a a binary result that indicates whether the criterion was satisfied (e.g., or a non-binary numeric or categorical result that indicates an extent to which the criterion was satisfied).

Process 600 proceeds to block 610 and performs blocks 610-620 for each criterion in the set of criteria. At block 610, an initial weight for a first criterion of the set of criteria is identified. When the criterion includes or is an inclusion criterion, the initial weight can indicate an importance of satisfaction of the criterion for inclusion in the investigatory event. When the criterion is an exclusion criterion, the initial weight can indicate an importance of satisfaction of the criterion for exclusion in the investigatory event.

At block 615, an eligibility-indicator value is generated for each entity. The eligibility-indicator value can indicate whether the criterion is satisfied with respect to the entity. The eligibility-indicator value can be determined based on electronic entity data retrieved for the entity. For example, the eligibility-indicator value can be set to 1 when the criterion is satisfied and 0 otherwise. In some instances, the electronic entity data may lack data for one or more fields to be assessed in the criterion. In these instances, the eligibility-indicator value may be set to (for example) a value indicating that the criterion is not satisfied or a value indicating that the criterion was not assessed (e.g., a default value, which may include an average, median or mode value across a larger set of entities).

At block 620, a size of a subset of entities for which the criterion is satisfied is identified. For example, the size can include a number of entities or a fraction of the set of entities for which the corresponding eligibility-indicator value was satisfied. Process 600 can then return to block 610, such that each of blocks 610-620 is performed for each criteria.

At block 625, a score is identified for each entity of the set of entities. The score can be generated to be based on the initial weights for each of the set of criteria, the eligibility-indicator values for each of the set of criteria, and the size of the subsets as identified for each of the set of criteria. In some instances, each initial weight is adjusted based on the subset size. For example, an adjustment factor can be applied to the initial weight that is anti-correlated with a portion of the population for which the criterion is satisfied. As another example, a relationship between the factor and the portion can be defined to be low (e.g., zero) when the criterion is satisfied for either a larger portion of the population or a small portion of the population (e.g., and having a high weight when the portion is 50%). Thus, even if a criterion is assigned an initial weight that is very high, if the criterion is satisfied for the vast majority of entities, an adjusted weight may be rather low.

As one specific illustration, an entity score for entity i can be defined based on the following approach:

A two criteria matrix $C_{m \times 2}$ can be defined with m=#Criteria and where $C_{\cdot 1}$ is a column vector indicating Must inclusion criterion and $C_{\cdot 2}$ is a column vector indicating Must exclusion criterion. $D_{m \times 2}$ can be defined where $D_{\cdot 1}$ is a column vector indicating weighted inclusion criterion and $D_{\cdot 2}$ is a column vector indicating weighted exclusion criterion. An entity-criteria matching matrix, $M_{p \times m}$ is defined with p=#Entities, where $M_{i,j}$ is a binary indicator for entity i satisfying criterion j. A leverage offset m-vector, l, is defined for the criteria to correspond to the proportion of entities which meet the $j^{th}$ criterion, such that:

$$l_j = \frac{\sum_{i=1}^{p} M_{i,j}}{p}.$$

An adjusted entity-criteria matching matrix, $M_{p \times m}^*$, can be defined where:

$M_{i,j}^* = M_{i,j} - l_j$

A criterion-satisfaction matrix, S, can be defined as:

$S = MC$ where $S_{\cdot 1}$ is a column vector specifying the number of satisfied Must inclusion criteria per entity and $S_{\cdot 2}$ is a column vector specifying the number of satisfied Must exclusion criteria per entity.

An intermediate score matrix, T, can be defined as:

$T = M^*D$ where $T_{\cdot 1}$ is a column vector specifying the inclusion score for each entity and $T_{\cdot 2}$ is a column vector specifying the exclusion score for each entity. A total score, $s_i$, can be computed for each entity i as:

$s_i = T_{i,1} - T_{i,2}$

This has advantageous statistical properties, such as $E[s_i] = 0$ and the variance being easily computable for each vector based on the l vector:

$$\mathrm{var}(s_i) = \sum_{j=1}^{m} w_j^2 l_j (1 - l_j)$$

where $w_j$ is the criteria weight for the $j^{th}$ criterion.

At block 630, data corresponding to the scores is output. For example, the score for each of one or more or all of the set of entities can be locally presented or transmitted to another device. In some instances, the score(s) for one or more entities are evaluated based on a predefined or learned threshold to identify which entities of the set of entities are eligible for a given investigatory event.

In some instances, it may be difficult for an investigator to identify thresholds for event criteria and/or weights. The investigator may have a general idea of entity characteristics that are desirable but struggle to identify cutoffs that reasonably impact a size of a potential entity pool yet maintain a support for the rationale of using the characteristic. One approach is to reduce a reliance on binary decision-making and instead use a multi-factor graded assessment to evaluate the complex combinations of characteristics observed across an entity population pool.

Figure 7:
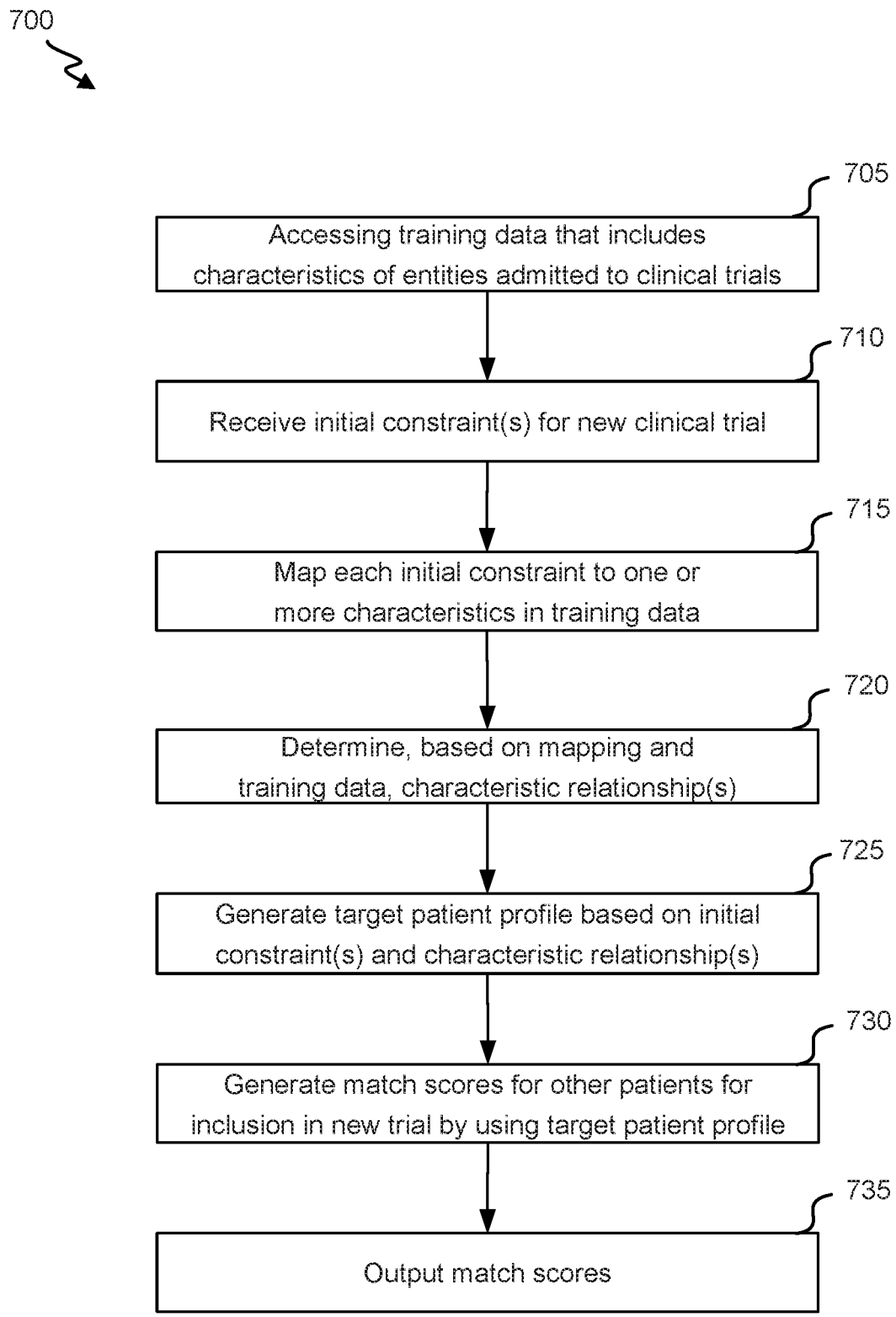
FIG. 7 shows a flowchart of a process for generating match scores during an assessment for investigatory-event eligibility in accordance with some embodiments.

FIG. 7 shows a flowchart of a process 700 for generated match scores during an assessment for investigatory-event eligibility in accordance with some embodiments. Process 700 begins at block 705 where training data is accessed. The training data can include characteristics of entities admitted to one or more investigatory events. The training data can further identify one or more investigatory-event results for each entity. The one or more investigatory-event results may indicate (for example) whether the entity completed participation in the investigatory event, whether the entity experienced any adverse events (e.g., and what they were), an efficacy result associated with the investigatory event and entity, and/or a clinical-investigator post hoc characterization pertaining to the entity (e.g., whether the entity was an outlier, excluded from at least one analysis, etc.).

At block 710 one or more initial constraints (e.g., included in one or more preliminary criteria groups or one or more actual criteria groups) for a new investigatory event are received. The one or more initial constraints may be identified based on input from an investigator (e.g., and/or received from an investigator system). The initial constraints may include one or more soft constraints and potentially one or more hard constraints. Each of one, more or all of the initial constraints may be associated with a definition of an assessment to be performed to generate a binary result (e.g., for any hard constraint and potentially for each of one or more soft constraints) or a non-binary result (e.g., a numeric result along a continuum).

At block 715, each initial constraint of the one or more initial constraints is mapped to one or more characteristics in the entity population data. For example, each field assessed in the initial constraint may be identified, and corresponding one or more characteristics can be identified. For example, an initial constraint may indicate that entities with high blood pressure are desirable for an investigatory event, and a characteristic identified at block 715 can include a blood pressures reading. As another example, an initial constraint may indicate that entities that are physically fit are desirable for an investigatory event, and characteristics identified at block 715 can include a body-mass index, weight and height.

At block 720, based on the mapping and the training data, one or more characteristic relationships are determined. For example, a characteristic relationship may identify that another characteristic is correlated with at least one of the one or more characteristics identified for an initial constraint. To illustrate, high blood pressure readings may be correlated with obesity and/or older entities. As another illustration, obesity may be correlated with a defined (e.g., open-ended) body mass index range and/or defined (e.g., open-ended) blood glucose level range. The one or more characteristic relationships can be generated based on machine learning, which may assign a weight to one or more connections and/or intermediate nodes associated with various characteristic combinations.

At block 725, a target entity profile is generated based on the one or more initial constraints and based on the one or more characteristic relationships. The target entity profile can identify a set of target characteristics. In some instances, the target entity profile can include at least one characteristic not expressly identified in the one or more initial constraints. In some instances, the target entity profile identifies a specific value or targeted range of values for at least one characteristic that is more precise than a value constraint included in the one or more initial constraints. The target entity profile may be identified by analyzing the combination of characteristics associated with entities that closely matched the one or more initial constraints.

At block 730, a match score is generated for each of one or more other entities based on the target profile and electronic entity data. The match score can correspond to an indication of degree to which the other entity matches eligibility criterion for a new investigatory event. For example, the target entity may be a male of age 30 having a weight of 160 having been diagnosed with diabetes six months ago. A given entity may be a female of age 30 having a weight of 140 having been diagnosed with diabetes a year ago. An extent to which each factor (sex, age, weight and time since diagnosis) can be used in combination with a weight of the characteristic to generate the match score. The weight of the characteristic may be determined based on learning and/or initial constraints.

At block 735, the match score(s) are output. For example, the match score for each of one or more or all of the other entities can be locally presented or transmitted to another device. In some instances, the score(s) for one or more of the other entities are evaluated based on a predefined or learned (e.g., relative or absolute) threshold to identify which entities of the set of entities are eligible for a given investigatory event.

Figure 8:
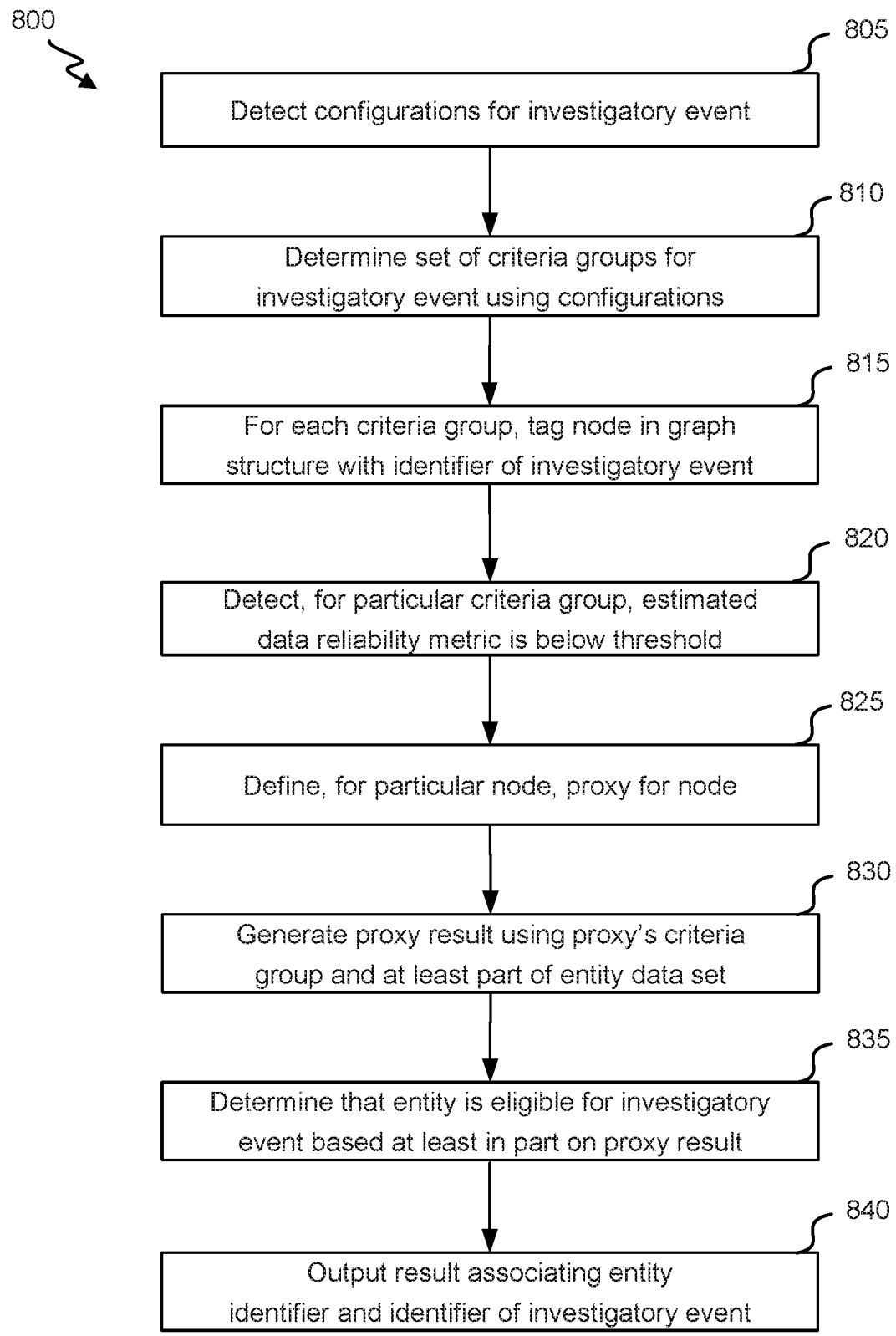
FIG. 8 shows a flowchart of a process for defining and using proxy nodes in a graph structure to facilitate investigatory-event mappings in accordance with some embodiments.

FIG. 8 shows a flowchart of a process 800 for defining and using proxy nodes in a graph structure to facilitate investigatory-event mappings in accordance with some embodiments. Process 800 begins at block 805 where a set of configurations for an investigatory event are detected. The set of configurations can be detected (for example) by extracting the set of configurations from a communication or file received from a user device; by detecting input provided via a local or remote interface; and/or by identifying one or more outputs of an artificial-intelligence technique that has automatically identified at least one of the set of configurations. The set of configurations may identify (for example) one or more constraints, specifications and/or criteria for accepting an entity to the investigatory event and/or for selecting the entity for further review (e.g., semi-automatic or manual review).

At block 810, a set of criteria groups for the investigatory event is determined using the set of configurations. Block 810 can include (for example) transforming each configuration (or all configurations) to be in a particular format, syntax or structure. The set of configurations can be transformed into a set of key-value pairs. In some instances, each of the set of configurations is transformed into a corresponding key-value pair. For example, a key may be identified for each configuration based on (for example) a field identifier associated with the identifier, a structure of the set of configurations, a previously detected input identifying the key, etc. The value may be set to be equal to the configuration or to be determined based on the configuration (e.g., by identifying which of multiple ranges a numeric configuration reside).

At block 815, for each criteria group of the set of criteria groups, a node in a graph structure is tagged with an identifier of the investigatory event. For example, a data object representing the node can be updated to include an identifier of the investigatory event or a pointer to a data object representing the investigatory event.

At block 820, it can be detected that an estimated data-reliability metric associated with a particular node (configured with a particular criteria group) is below a predefined threshold. More specifically, the estimated data-reliability metric can correspond to an estimate of the reliability, availability and/or accuracy of each of one or more types of data that are to be assessed via the particular criteria group. The estimated data-reliability metric can be generated using a plurality of entity data sets and potentially one or more true values or results associated with the entity data sets. For example, the metric may be generated based on a percentage of the plurality of entity data sets that include each of one, more, or all types of data that are to be assessed via the particular criteria group, a variability of values of a data type of the one or more types of data, a characteristic of a distribution of values of a data type of the one or more types of data, a variation in formats of values of a data type of the one or more types of data, a degree to which values of a data type of the one or more types of data match subsequently identified true values for the data types (e.g., as indicated via post-processing input or data detection) and/or a degree to which values of a data type of the one or more types of data are related to final entity selection.

The threshold against which the estimated data-reliability metric is compared can be (for example) numeric or categorical. For example, a type of data may be configured such that a value can be set to any of a predefined set of category identifiers. The set of category identifiers can be associated with a scale (e.g., very low, low, medium, high, very high), even if they are non-numeric. Thus, a threshold can be set using the category (e.g., threshold=medium). The threshold may be identified using (for example) a machine-learning model, clustering algorithm, and/or support vector machine. In some instances, the threshold is defined by user input.

Upon detecting that the estimated data-reliability metric is below the threshold for the particular criteria group of the particular node, a proxy for the particular node can be defined. The proxy can be defined to estimate a processing result of the particular criteria group based on a processing result of another criteria group (with which another node is configured). The other node can include an existing node or node that is to be generated and integrated into the graph structure. The other criteria group can be configured to assess one or more values of one or more different data types. The one or more different data types may be (for example) associated with one or more estimated data reliability metrics that are not below the threshold. In some instances, the proxy is defined based on multiple other nodes corresponding to multiple other criteria groups. For example, the proxy may be defined to correspond to a first node that includes a logic-operator criteria group that is based on evaluations of criteria groups of two or more other proxy nodes.

The proxy can be defined based on (for example) assessing multiple empirical data sets to identify dependencies and relationships between different data types. As another example, the proxy can be defined by identifying which data types from entity data sets are predictive of subsequently identified true values or true results (e.g., a true result of a criteria group or a true indication as to whether an entity was selected for an investigatory event). The true values and/or results can be identified from user input, communications, data extractions, etc. The proxy can be defined by executing (or training) a machine-learning model, applying a clustering algorithm, applying regression technique or applying distance-based technique. In some instances, execution or application of a model, algorithm or technique can generate one or more weights and/or coefficients—each of which may be associated with one or more data types. The proxy may then be defined based on the one or more weights and/or coefficients. For example, a proxy node may be configured to generate a weighted sum of outputs from two or more other nodes and to then compare the weighted sum to one or more thresholds.

The proxy for the node can then be used to evaluate entity data sets to determine whether an identifier associated with a given entity data set is to be mapped to an identifier of the investigatory event. One or more proxy nodes can be integrated into a path for the investigatory event. For example, a portion of a path that connected to the particular node may be changed to instead connect to a proxy node. Thus, the proxy's criteria group can be evaluated at a same position in the path as was identified for the particular node.

At block 830, a proxy result is generated using the criteria group(s) of the proxy node(s) and at least part of an entity data set. Block 830 may be performed subsequent to determining (for example) that each of one or more previously evaluated criteria nodes of each of one or more nodes higher in a path were satisfied. The proxy result may be generated in lieu of evaluating the particular criteria group and may use the portion(s) of the entity data set that include values of the data types called for in the proxy's criteria group(s).

The proxy result may (but need not) indicate whether a trajectory is to be extended. For example, if a proxy node feeds to an "OR" logic node, the trajectory may potentially extend even if the proxy result indicates that the proxy's criteria group is not satisfied. Conversely, if a proxy node feeds to an "AND" logic node, the trajectory may potentially not extend even if the proxy result indicates that the proxy's criteria group is satisfied. In some instances, the proxy result solely determines whether the trajectory extends to a next node.

At block 835, it is determined that an entity corresponding to the entity data set is eligible for (e.g., and thus is mapped to) the investigatory event based at least in part on the proxy result. For example, the determination may be made in response to detecting that a trajectory of the entity has extended to an end node corresponding to the investigatory event.

At block 840, a result associating an identifier of the entity with an identifier of the investigatory event is output. For example, the result may include identifiers of all entities mapped to the investigatory event and may be output to (e.g., transmitted to) or on (e.g., presented at) a user device associated with the investigatory event. As another example, the result may include identifiers of all investigatory events mapped to the event and may be output to or on a user device associated with the entity (e.g., or a corresponding medical entity).

It will be appreciated that variations of process 800 are contemplated. For example, rather than generally determining whether an estimated data reliability metric is below a threshold for a particular criteria group (e.g., in the context of a specific investigatory event or across investigatory events), the determination may be made on an iteration-specific basis. For example, block 820 may include determining whether a value of a given datatype is present for a particular entity data set, and process 800 may proceed to block 825 only in instances in which the value is not present. As other examples, block 820 may include determining whether a value of a given data type exceeds a threshold (e.g., a multiple of a standard deviation of a distribution of values plus an average value) or has a particular format, and process 800 may proceed only in instances in which the threshold is exceeded or the value has the particular format.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
    detecting a set of configurations for detecting identifiers corresponding to a particular investigatory event;
    determining, using the set of configurations, a set of criteria groups for the particular investigatory event;
    for each criteria group of the set of criteria groups, tagging a node in a graph structure with an identifier of the particular investigatory event, the node configured with the criteria group, the graph structure connecting a set of nodes via a set of edges, each edge of the set of edges connecting two nodes of the set of nodes, the set of nodes including a plurality of end nodes, each node of the plurality of end nodes identifying an investigatory event;
    for a particular criteria group of the set of criteria groups:
        identifying a data type corresponding to the particular criteria group, wherein the particular criteria group specifies an assessment of data corresponding to the data type;
        accessing previous entity data corresponding to a plurality of entities, the previous entity data indicating an extent to which data corresponding to the data type was previously available in association with the plurality of entities;
        defining a historical availability of the data type by:
            identifying multiple data records corresponding to multiple other entities; and
            determining the percentage of the multiple data records that include a value of the data type;
        generating, based on the previous entity data, an estimated data-availability metric associated with a particular node configured with the particular criteria group, the estimated data-availability metric indicating an estimated extent to which the data type is available for the assessment via the particular criteria group based on the historical availability of the data type;
        detecting that the estimated data-availability metric is below a predefined threshold; and
        as a result of detecting that the estimated data-availability metric is below the predefined threshold, defining, for the particular node, a proxy node for the particular node, wherein the proxy node is configured with another criteria group and is defined to estimate, based on another type of data of the plurality of entity data sets, a processing result of the other criteria group;
    receiving an entity data set;
    generating a proxy result by evaluating the other criteria group of the proxy node using another type of data of the entity data set;
    determining that an entity corresponding to the entity data set is eligible for the particular investigatory event based at least in part on the proxy result; and
    outputting a result that associates an identifier of the entity and an identifier of the particular investigatory event.

2. The computer-implemented method of claim 1, wherein the proxy node for the particular node is defined based on an output generated using an artificial-intelligence algorithm that identifies one or more data types predictive of an output of the particular node.

3. The computer-implemented method of claim 1, further comprising, for the particular criteria group:
    receiving selection data that identifies a set of entities, the set of entities including:
        a first subset of the set of entities that were selected for one or more other investigatory events, wherein, for each other investigatory event of the one or more other investigatory events, an identifier of the other investigatory event was also linked to the particular node; and
        a second subset of the set of entities that were not selected for the one or more other investigatory events;
    retrieving a plurality of attributes that corresponds to the set of entities; and
    determining, using the plurality of attributes and using a machine-learning model, that values of one or more types of attributes correspond to processing results of the particular criteria group;
    wherein the other criteria group of the proxy node processes at least one of the one or more types of attributes.

4. The computer-implemented method of claim 3, wherein the determination, using the plurality of attributes and using the machine-learning model, that values of the one or more types of attributes correspond to processing results of the particular criteria group includes:
    training the machine-learning model to learn a set of machine-learning parameters, wherein one or more of the set of machine-learning parameters includes, for each of the set of attribute types, a weight or coefficient, the set of attribute types including the one or more types of attributes;
    detecting, for each of the one or more types of attributes, that the weight or coefficient of the attribute exceeds a predefined threshold.

5. The computer-implemented method of claim 1, further comprising, for each criteria group of the set of criteria groups:

querying the graph structure to determine whether the graph structure includes any existing node configured with the criteria group; and when it is determined that the graph structure does not include any existing node configured with the criteria group, updating the graph structure to include a new node configured with the criteria group, wherein the tagging includes tagging the new node with the identifier of the particular investigatory event.

6. The computer-implemented method of claim 1, further comprising:

generating, for each criteria group of a plurality of additional criteria groups of the set of criteria groups, an additional processing result of the criteria group using another at least part of the entity data set, wherein the determination that the entity is eligible for the investigatory event is further based on the additional processing results.

7. The computer-implemented method of claim 1, wherein the estimated data-availability metric is based on a fraction of entities for which a value for a type of entity attribute is not included in an entity data set, the particular criteria group being configured to process the type of entity attribute.

8. The computer-implemented method of claim 1, further comprising:

querying one or more data structures using an identifier of the data type, wherein the previous entity data was received in response to the query.

9. The computer-implemented method of claim 1, wherein defining the proxy node for the particular node further comprises:

defining a set of additional proxy nodes for the particular node; and using the proxy node and the set of additional proxy nodes collectively as an overall proxy to generate the proxy result for the entity.

10. The computer-implemented method of claim 1, wherein the previous entity data includes previous trajectory data, and wherein generating the estimated data-availability metric further comprises:

identifying, based on the previous trajectory data, a set of trajectories that extend to a node configured with a criteria group that depends on an evaluation based on the data type;

identifying, based on the previous trajectory data, a subset of the set of trajectories for which the trajectory extends through the node; and determining the estimated data-availability metric based on a size of the subset and a size of the set.

11. A system comprising:

one or more data processors; and a non-transitory computer readable storage medium containing instructions which when executed on the one or more data processors, cause the one or more data processors to perform actions including:

detecting a set of configurations for detecting identifiers corresponding to a particular investigatory event;

determining, using the set of configurations, a set of criteria groups for the investigatory event;

for each criteria group of the set of criteria groups, tagging a node in a graph structure with an identifier of the particular investigatory event, the node configured with the criteria group, the graph structure connecting a set of nodes via a set of edges, each edge of the set of edges connecting two nodes of the set of nodes, the set of nodes including a plurality of end nodes, each node of the plurality of end nodes identifying the investigatory event;

for a particular criteria group of the set of criteria groups:

identifying a data type corresponding to the particular criteria group, wherein the particular criteria group specifies an assessment of data corresponding to the data type;

accessing previous entity data corresponding to a plurality of entities, the previous entity data indicating an extent to which data corresponding to the data type was previously available in association with the plurality of entities;

defining a historical availability of the data type by:

identifying multiple data records corresponding to multiple other entities; and determining the percentage of the multiple data records that include a value of the data type;

generating, based on the previous entity data, an estimated data-availability metric associated with a particular node configured with the particular criteria group, the estimated data-availability metric indicating an estimated extent to which the data type is available for the assessment via the particular criteria group based on the historical availability of the data type;

detecting that the estimated data-availability metric is below a predefined threshold; and as a result of detecting that the estimated data-availability metric is below the predefined threshold, defining, for the particular node, a proxy node for the particular node, wherein the proxy node is configured with another criteria group and is defined to estimate, based on another type of data of the plurality of entity data sets, a processing result of the other criteria group;

receiving an entity data set;

generating a proxy result by evaluating the other criteria group of the proxy node using another type of data of the entity data set;

determining that an entity corresponding to the entity data set is eligible for the particular investigatory event based at least in part on the proxy result; and outputting a result that associates an identifier of the entity and an identifier of the particular investigatory event.

12. The system of claim 11, wherein the proxy node for the particular node is defined based on an output generated using an artificial-intelligence algorithm that identifies one or more data types predictive of an output of the particular node.

13. The system of claim 11, wherein the actions further include, for the particular criteria group:

receiving selection data that identifies a set of entities, the set of entities including:

a first subset of the set of entities that were selected for one or more other investigatory events, wherein, for each other investigatory event of the one or more other investigatory events, an identifier of the other investigatory event was also linked to the particular node; and a second subset of the set of entities that were not selected for the one or more other investigatory events;

retrieving a plurality of attributes that corresponds to the set of entities; and determining, using the plurality of attributes and using a machine-learning model, that values of one or more types of attributes correspond to processing results of the particular criteria group;

wherein the other criteria group of the proxy node processes at least one of the one or more types of attributes.

14. The system of claim 13, wherein the determination, using the plurality of attributes and using the machine-learning model, that values of the one or more types of attributes correspond to processing results of the particular criteria group includes:

training the machine-learning model to learn a set of machine-learning parameters, wherein one or more of the set of machine-learning parameters includes, for each of the set of attribute types, a weight or coefficient, the set of attribute types including the one or more types of attributes;

detecting, for each of the one or more types of attributes, that the weight or coefficient of the attribute exceeds a predefined threshold.

15. The system of claim 11, wherein the actions further include, for each criteria group of the set of criteria groups:

querying the graph structure to determine whether the graph structure includes any existing node configured with the criteria group; and when it is determined that the graph structure does not include any existing node configured with the criteria group, updating the graph structure to include a new node configured with the criteria group, wherein the tagging includes tagging the new node with the identifier of the particular investigatory event.

16. The system of claim 11, wherein the actions further include:

generating, for each criteria group of a plurality of additional criteria groups of the set of criteria groups, an additional processing result of the criteria group using another at least part of the entity data set, wherein the determination that the entity is eligible for the particular investigatory event is further based on the additional processing results.

17. The system of claim 11, wherein the estimated data-availability metric is based on a fraction of entities for which a value for a type of entity attribute is not included in an entity data set, the particular criteria group being configured to process the type of entity attribute.

18. A computer-program product tangibly embodied in a non-transitory machine-readable storage medium, including instructions configured to cause one or more data processors to perform actions including:

detecting a set of configurations for detecting identifiers corresponding to a particular investigatory event;

determining, using the set of configurations, a set of criteria groups for the particular investigatory event;

for each criteria group of the set of criteria groups, tagging a node in a graph structure with an identifier of the particular investigatory event, the node configured with the criteria group, the graph structure connecting a set of nodes via a set of edges, each edge of the set of edges connecting two nodes of the set of nodes, the set of nodes including a plurality of end nodes, each node of the plurality of end nodes identifying the investigatory event;

for a particular criteria group of the set of criteria groups:
identifying a data type corresponding to the particular criteria group, wherein the particular criteria group specifies an assessment of data corresponding to the data type;

accessing previous entity data corresponding to a plurality of entities, the previous entity data indicating an extent to which data corresponding to the data type was previously available in association with the plurality of entities;

defining a historical availability of the data type by:
identifying multiple data records corresponding to multiple other entities; and
determining the percentage of the multiple data records that include a value of the data type;

generating, based on the previous entity data, an estimated data-availability metric associated with a particular node configured with the particular criteria group, the estimated data-availability metric indicating an estimated extent to which the data type is available for the assessment via the particular criteria group based on the historical availability of the data type;

detecting that the estimated data-availability metric is below a predefined threshold; and as a result of detecting that the estimated data-availability metric is below the predefined threshold, defining, for the particular node, a proxy node for the particular node, wherein the proxy node is configured with another criteria group and is defined to estimate, based on another type of data of the plurality of entity data sets, a processing result of the other criteria group;

receiving an entity data set;

generating a proxy result by evaluating the other criteria group of the proxy node using another type of data of the entity data set;

determining that an entity corresponding to the entity data set is eligible for the particular investigatory event based at least in part on the proxy result; and outputting a result that associates an identifier of the entity and an identifier of the particular investigatory event.

19. The computer-program product of claim 18, wherein the proxy node for the particular node is defined based on an output generated using an artificial-intelligence algorithm that identifies one or more data types predictive of an output of the particular node.

20. The computer-program product of claim 18, wherein the actions further include, for the particular criteria group:

receiving selection data that identifies a set of entities, the set of entities including:

a first subset of the set of entities that were selected for one or more other investigatory events, wherein, for each other investigatory event of the one or more other investigatory events, an identifier of the other investigatory event was also linked to the particular node; and a second subset of the set of entities that were not selected for the one or more other investigatory events;

retrieving a plurality of attributes that corresponds to the set of entities; and determining, using the plurality of attributes and using a machine-learning model, that values of one or more types of attributes correspond to processing results of the particular criteria group;

wherein the other criteria group of the proxy node processes at least one of the one or more types of attributes.

21. The computer-program product of claim 20, wherein the determination, using the plurality of attributes and using the machine-learning model, that values of the one or more types of attributes correspond to processing results of the particular criteria group includes:
 training the machine-learning model to learn a set of machine-learning parameters, wherein one or more of the set of machine-learning parameters includes, for each of the set of attribute types, a weight or coefficient, the set of attribute types including the one or more types of attributes;
 detecting, for each of the one or more types of attributes, that the weight or coefficient of the attribute exceeds a predefined threshold.

22. The computer-program product of claim 18, wherein the actions further include, for each criteria group of the set of criteria groups:
 querying the graph structure to determine whether the graph structure includes any existing node configured with the criteria group; and
 when it is determined that the graph structure does not include any existing node configured with the criteria group, updating the graph structure to include a new node configured with the criteria group, wherein the tagging includes tagging the new node with the identifier of the investigatory event.

23. The computer-program product of claim 18, wherein the estimated data-availability metric is based on a fraction of entities for which a value for a type of entity attribute is not included in an entity data set, the particular criteria group being configured to process the type of entity attribute.

\* \* \* \* \*